(12) United States Patent
Susin et al.

(10) Patent No.: US 11,759,496 B2
(45) Date of Patent: Sep. 19, 2023

(54) COMPOUNDS AND PHARMACEUTICAL USE THEREOF IN THE TREATMENT OF CANCER

(71) Applicant: Philippe Karoyan, Courson-Monteloup (FR)

(72) Inventors: Santos A. Susin, Paris (FR); Philippe Karoyan, Paris (FR); Hélène Merle-Beral, Paris (FR)

(73) Assignee: Philippe Karoyan, Courson-Monteloup (FR)

( * ) Notice: Subject to any disclaimer, the term of this patent is extended or adjusted under 35 U.S.C. 154(b) by 0 days.

(21) Appl. No.: 16/099,974

(22) PCT Filed: May 10, 2017

(86) PCT No.: PCT/EP2017/061223
§ 371 (c)(1),
(2) Date: Nov. 8, 2018

(87) PCT Pub. No.: WO2017/194627
PCT Pub. Date: Nov. 16, 2017

(65) Prior Publication Data
US 2019/0144501 A1     May 16, 2019

(30) Foreign Application Priority Data

May 10, 2016   (EP) .................... 16305541

(51) Int. Cl.
*A61K 38/00*   (2006.01)
*A61K 38/08*   (2019.01)
*C07K 7/06*    (2006.01)
*A61P 35/00*   (2006.01)

(52) U.S. Cl.
CPC .............. *A61K 38/08* (2013.01); *A61P 35/00* (2018.01); *C07K 7/06* (2013.01)

(58) Field of Classification Search
CPC combination set(s) only.
See application file for complete search history.

(56) References Cited

U.S. PATENT DOCUMENTS

| 4,966,848 | A | * | 10/1990 | Smith | .................. | C12N 9/1029 435/193 |
| 5,223,421 | A | * | 6/1993 | Smith | .................. | C12N 9/1029 435/193 |
| 5,837,218 | A | * | 11/1998 | Peers | .................. | A61K 51/088 424/1.69 |
| 9,198,949 | B2 | * | 12/2015 | Susin | .................. | C07K 14/78 |

FOREIGN PATENT DOCUMENTS

| WO | 2013/182650 A1 | 12/2013 |
| WO | 2015/086727 A2 | 6/2015 |

OTHER PUBLICATIONS

International Search Report dated Aug. 21, 2017, issued in corresponding International Application No. PCT/EP2017/061223, filed May 10, 2017, 4 pages.
Written Opinion dated Aug. 21, 2017, issued in corresponding International Application No. PCT/EP2017/061223, filed May 10, 2017, 8 pages.

* cited by examiner

*Primary Examiner* — Thomas S Heard
(74) *Attorney, Agent, or Firm* — ArentFox Schiff LLP

(57) ABSTRACT

The present invention relates to a compound or a pharmaceutical salt thereof comprising a hexapeptide sequence of formula (I), its method of synthesis and its use in anticancer therapy. The invention also relates to a pharmaceutical composition for use in the treatment of cancer comprising at least one soluble peptide according to the invention or at least one acid nucleic according to the invention or at least one expression vector according to the invention, or at least one host cell according to the invention and a pharmaceutically acceptable carrier.

Figure 3:
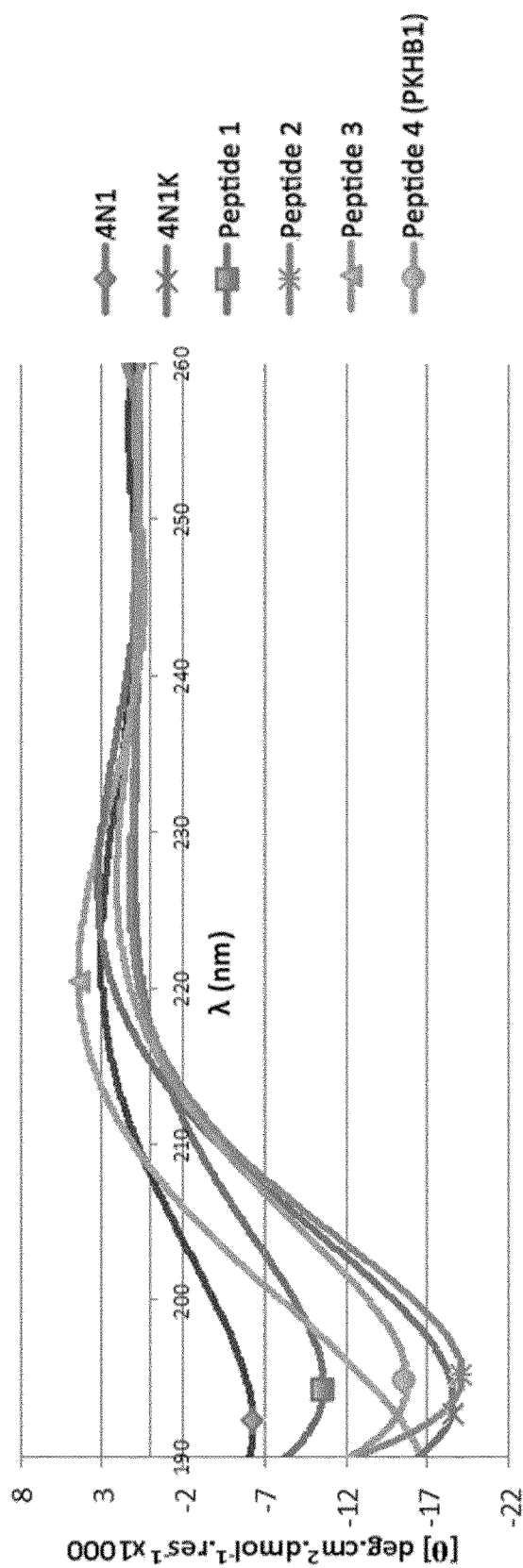

5 Claims, 3 Drawing Sheets
Specification includes a Sequence Listing.

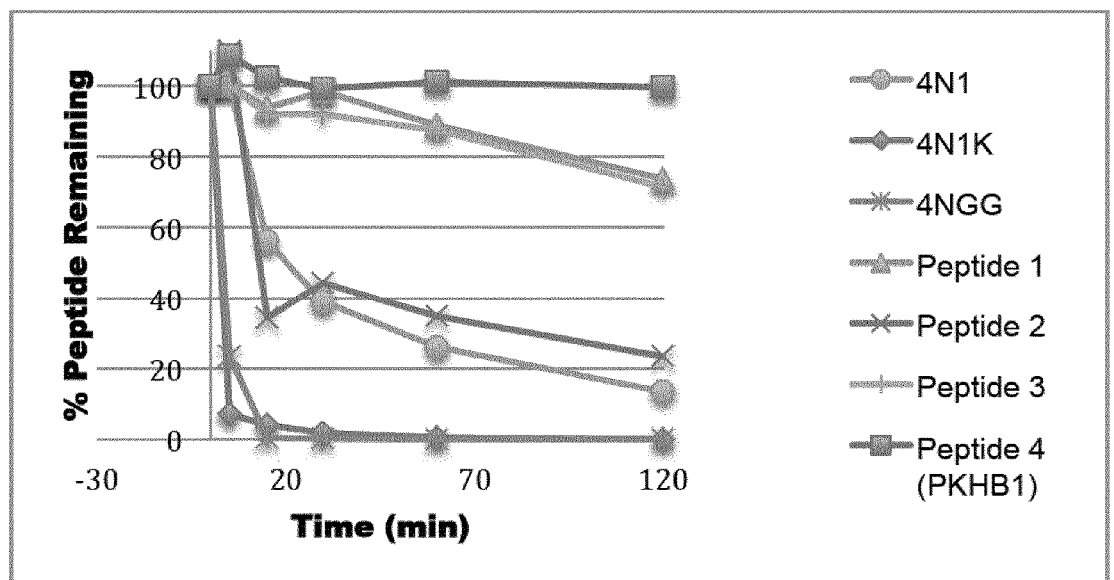
FIG 1
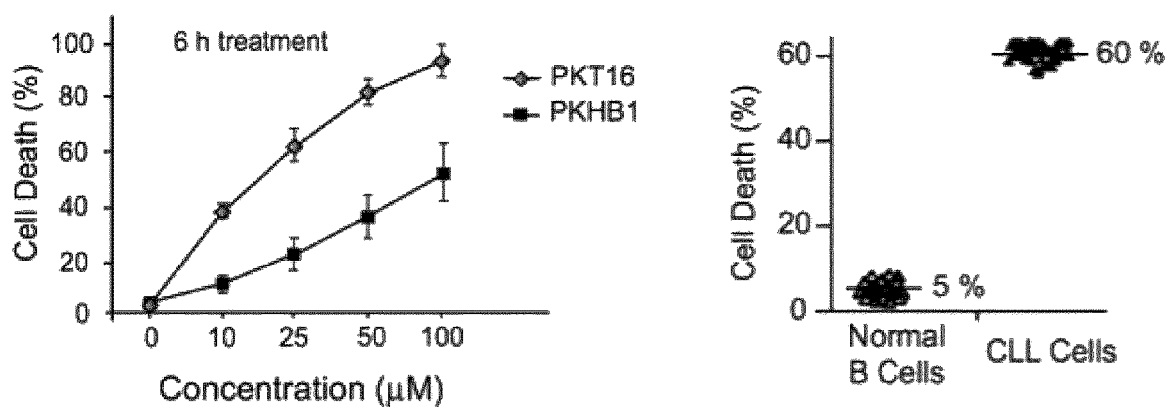
FIG 2A
FIG 2B

SEQUENCE LISTING

```
<160> NUMBER OF SEQ ID NOS: 42

<210> SEQ ID NO 1
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Xaa at position 5 represents Norleucine

<400> SEQUENCE: 1

Phe Tyr Val Val Xaa Trp
1               5
```

```
<210> SEQ ID NO 2
<211> LENGTH: 6
<212> TYPE: PRT
<213> ORGANISM: Artificial Sequence
<220> FEATURE:
<223> OTHER INFORMATION: Synthetic

<400> SEQUENCE: 2

Phe Tyr Val Val Ile Trp
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic

<400> SEQUENCE: 3

Phe Tyr Val Val Lys Trp
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic

<400> SEQUENCE: 4

Phe Tyr Val Val Leu Trp
1               5

<210> SEQ ID NO 5
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa at position 4 represents Norleucine

<400> SEQUENCE: 5

Tyr Val Val Xaa
1

<210> SEQ ID NO 6
<211> LENGTH: 10
<212> TYPE: PRT
<213> ORGANISM: Artificial Sequence
<220> FEATURE:
<223> OTHER INFORMATION: Synthetic

<400> SEQUENCE: 6

Lys Arg Phe Tyr Gly Gly Met Trp Lys Lys
1               5                   10

<210> SEQ ID NO 7
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(8)
<223> OTHER INFORMATION: ACETYLATION N-terminal and AMIDATION C-terminal
```

```
<400> SEQUENCE: 7

Arg Phe Tyr Val Val Met Trp Lys
1               5

<210> SEQ ID NO 8
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(10)
<223> OTHER INFORMATION: ACETYLATION N-terminal and AMIDATION C-terminal

<400> SEQUENCE: 8

Lys Arg Phe Tyr Val Val Met Trp Lys Lys
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Amino acid at position 1 is in the
      D-configuration
<220> FEATURE:
<221> NAME/KEY: MISC_FEATURE
<222> LOCATION: (10)..(10)
<223> OTHER INFORMATION: Amino acid at position 10 is in the
      D-configuration

<400> SEQUENCE: 9

Lys Arg Phe Tyr Val Val Met Trp Ala Lys
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Amino acid at postiion 1 is in the
      D-configuration
<220> FEATURE:
<221> NAME/KEY: MISC_FEATURE
<222> LOCATION: (10)..(10)
<223> OTHER INFORMATION: Amino acid at postiion 10 is in the
      D-configuration

<400> SEQUENCE: 10

Lys Ala Phe Tyr Val Val Met Trp Lys Lys
1               5                   10

<210> SEQ ID NO 11
<211> LENGTH: 8
<212> TYPE: PRT
<213> ORGANISM: Artificial Sequence
<220> FEATURE:
<223> OTHER INFORMATION: Syntheic
<220> FEATURE:
<221> NAME/KEY: MISC_FEATURE
<222> LOCATION: (1)..(1)
<223> OTHER INFORMATION: Arg at position 1 is a homo beta 2 Arg
```

```
<220> FEATURE:
<221> NAME/KEY: MISC_FEATURE
<222> LOCATION: (8)..(8)
<223> OTHER INFORMATION: Lys at position 8 is a homo beta 3 Lys

<400> SEQUENCE: 11

Arg Phe Tyr Val Val Met Trp Lys
1               5

<210> SEQ ID NO 12
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Amino acid at postiion 1 is in the
      D-configuration
<220> FEATURE:
<221> NAME/KEY: MISC_FEATURE
<222> LOCATION: (7)..(7)
<223> OTHER INFORMATION: Xaa at  postiion 7 represents Norleucine
<220> FEATURE:
<221> NAME/KEY: MISC_FEATURE
<222> LOCATION: (10)..(10)
<223> OTHER INFORMATION: Amino acid at postiion 10 is in the
      D-configuration

<400> SEQUENCE: 12

Lys Arg Phe Tyr Val Val Xaa Trp Lys Lys
1               5                   10

<210> SEQ ID NO 13
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(6)
<223> OTHER INFORMATION: AMIDATION C-terminal
<220> FEATURE:
<221> NAME/KEY: MISC_FEATURE
<222> LOCATION: (5)..(5)
<223> OTHER INFORMATION: Xaa at position 5 represents Norleucine

<400> SEQUENCE: 13

Phe Tyr Val Val Xaa Trp
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(6)
<223> OTHER INFORMATION: ACETYLATION N-terminal
<220> FEATURE:
<221> NAME/KEY: MISC_FEATURE
<222> LOCATION: (5)..(5)
<223> OTHER INFORMATION: Xaa at position 5 represents Norleucine

<400> SEQUENCE: 14

Phe Tyr Val Val Xaa Trp
1               5
```

```
<210> SEQ ID NO 15
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(6)
<223> OTHER INFORMATION: ACETYLATION N-terminal and AMIDATION C-terminal
<220> FEATURE:
<221> NAME/KEY: MISC_FEATURE
<222> LOCATION: (5)..(5)
<223> OTHER INFORMATION: Xaa at position 5 represents Norleucine

<400> SEQUENCE: 15

Phe Tyr Val Val Xaa Trp
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Amino acid at postiion 1 is in the
      D-configuration
<220> FEATURE:
<221> NAME/KEY: MISC_FEATURE
<222> LOCATION: (6)..(6)
<223> OTHER INFORMATION: Xaa at position 6 represents Norleucine
<220> FEATURE:
<221> NAME/KEY: MISC_FEATURE
<222> LOCATION: (8)..(8)
<223> OTHER INFORMATION: Amino acid at position 8 is in the
      D-configuration

<400> SEQUENCE: 16

Lys Phe Tyr Val Val Xaa Trp Lys
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(6)
<223> OTHER INFORMATION: AMIDATION C-terminal

<400> SEQUENCE: 17

Phe Tyr Val Val Lys Trp
1               5

<210> SEQ ID NO 18
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Amino acid at position 1 is in the
      D-configuration
```

```
<220> FEATURE:
<221> NAME/KEY: MISC_FEATURE
<222> LOCATION: (2)..(2)
<223> OTHER INFORMATION: Amino acid at position 2 is backbone-N-
      METHYLATION of the Arginine
<220> FEATURE:
<221> NAME/KEY: MISC_FEATURE
<222> LOCATION: (10)..(10)
<223> OTHER INFORMATION: Amino acid at position 10 is in the
      D-configuration

<400> SEQUENCE: 18

Lys Arg Phe Tyr Val Val Met Trp Lys Lys
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Amino acid at position 1 is in the
      D-configuration
<220> FEATURE:
<221> NAME/KEY: MISC_FEATURE
<222> LOCATION: (9)..(9)
<223> OTHER INFORMATION: Amino acid at position 9 is backbone-N-
      METHYLATION of the Lysine
<220> FEATURE:
<221> NAME/KEY: MISC_FEATURE
<222> LOCATION: (10)..(10)
<223> OTHER INFORMATION: Amino acid at position 10 is in the
      D-configuration

<400> SEQUENCE: 19

Lys Arg Phe Tyr Val Val Met Trp Lys Lys
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Amino acid at position 1 is in the
      D-configuration
<220> FEATURE:
<221> NAME/KEY: MISC_FEATURE
<222> LOCATION: (2)..(2)
<223> OTHER INFORMATION: Amino acid at position 2 is backbone-N-
      METHYLATION of the Arginine
<220> FEATURE:
<221> NAME/KEY: MISC_FEATURE
<222> LOCATION: (9)..(9)
<223> OTHER INFORMATION: Amino acid at position 9 is backbone-N-
      METHYLATION of the Lysine
<220> FEATURE:
<221> NAME/KEY: MISC_FEATURE
<222> LOCATION: (10)..(10)
<223> OTHER INFORMATION: Amino acid at position 10 is in the
      D-configuration

<400> SEQUENCE: 20

Lys Arg Phe Tyr Val Val Met Trp Lys Lys
1               5                   10
```

-continued

```
<210> SEQ ID NO 21
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Amino acid at position 1 is in the
      D-configuration
<220> FEATURE:
<221> NAME/KEY: MISC_FEATURE
<222> LOCATION: (2)..(2)
<223> OTHER INFORMATION: Amino acid at position 2 is backbone-N-
      METHYLATION of the Arginine
<220> FEATURE:
<221> NAME/KEY: MISC_FEATURE
<222> LOCATION: (7)..(7)
<223> OTHER INFORMATION: Xaa at position 7 represents Norleucine
<220> FEATURE:
<221> NAME/KEY: MISC_FEATURE
<222> LOCATION: (10)..(10)
<223> OTHER INFORMATION: Amino acid at position 10 is in the
      D-configuration

<400> SEQUENCE: 21

Lys Arg Phe Tyr Val Val Xaa Trp Lys Lys
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Amino acid at position 1 is in the
      D-configuration
<220> FEATURE:
<221> NAME/KEY: MISC_FEATURE
<222> LOCATION: (2)..(2)
<223> OTHER INFORMATION: Amino acid at position 2 is backbone-N-
      METHYLATION of the Arginine
<220> FEATURE:
<221> NAME/KEY: MISC_FEATURE
<222> LOCATION: (10)..(10)
<223> OTHER INFORMATION: Amino acid at position 10 is in the
      D-configuration

<400> SEQUENCE: 22

Lys Arg Phe Tyr Val Val Leu Trp Lys Lys
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Amino acid at position 1 is in the
      D-configuration
<220> FEATURE:
<221> NAME/KEY: MISC_FEATURE
<222> LOCATION: (2)..(2)
<223> OTHER INFORMATION: Amino acid at position 2 is backbone-N-
      METHYLATION of the Arginine
```

```
<220> FEATURE:
<221> NAME/KEY: MISC_FEATURE
<222> LOCATION: (10)..(10)
<223> OTHER INFORMATION: Amino acid at position 10 is in the
      D-configuration

<400> SEQUENCE: 23

Lys Arg Phe Tyr Val Val Ile Trp Lys Lys
1               5                   10

<210> SEQ ID NO 24
<211> LENGTH: 8
<212> TYPE: PRT
<213> ORGANISM: Artificial Sequence
<220> FEATURE:
<223> OTHER INFORMATION: Synthetic

<400> SEQUENCE: 24

Arg Phe Tyr Val Val Met Trp Lys
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(8)
<223> OTHER INFORMATION: ACETYLATION N-terminal and AMIDATION C-terminal

<400> SEQUENCE: 25

Arg Phe Tyr Val Val Met Trp Lys
1               5

<210> SEQ ID NO 26
<211> LENGTH: 10
<212> TYPE: PRT
<213> ORGANISM: Artificial Sequence
<220> FEATURE:
<223> OTHER INFORMATION: Synthetic

<400> SEQUENCE: 26

Lys Arg Phe Tyr Val Val Met Trp Lys Lys
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Amino acid at position 1 is in the
      D-configuration
<220> FEATURE:
<221> NAME/KEY: MISC_FEATURE
<222> LOCATION: (10)..(10)
<223> OTHER INFORMATION: Amino acid at position 10 is in the
      D-configuration

<400> SEQUENCE: 27

Lys Arg Phe Tyr Val Val Met Trp Lys Lys
1               5                   10
```

```
<210> SEQ ID NO 28
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Amino acid at position 1 is in the
      D-configuration
<220> FEATURE:
<221> NAME/KEY: MISC_FEATURE
<222> LOCATION: (10)..(10)
<223> OTHER INFORMATION: Amino acid at position 10 is in the
      D-configuration

<400> SEQUENCE: 28

Lys Ala Phe Tyr Val Val Met Trp Lys Lys
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Amino acid at postiion 1 is in the
      D-configuration
<220> FEATURE:
<221> NAME/KEY: MISC_FEATURE
<222> LOCATION: (6)..(6)
<223> OTHER INFORMATION: Amino acid at postiion 6 is backbone-N-
      METHYLATION of teh Valine
<220> FEATURE:
<221> NAME/KEY: MISC_FEATURE
<222> LOCATION: (10)..(10)
<223> OTHER INFORMATION: Amino acid at postiion 10 is in the
      D-configuration

<400> SEQUENCE: 29

Lys Arg Phe Tyr Val Val Met Trp Lys Lys
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Amino acid at position 1 is in the
      D-configuration
<220> FEATURE:
<221> NAME/KEY: MISC_FEATURE
<222> LOCATION: (5)..(5)
<223> OTHER INFORMATION: Amino acid at position 5 is backbone-N-
      METHYLATION of the Valine
<220> FEATURE:
<221> NAME/KEY: MISC_FEATURE
<222> LOCATION: (10)..(10)
<223> OTHER INFORMATION: Amino acid at position 10 is in the
      D-configuration

<400> SEQUENCE: 30

Lys Arg Phe Tyr Val Val Met Trp Lys Lys
1               5                   10
```

```
<210> SEQ ID NO 31
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Amino acid at position 1 is in the
      D-configuration
<220> FEATURE:
<221> NAME/KEY: MISC_FEATURE
<222> LOCATION: (4)..(4)
<223> OTHER INFORMATION: Amino acid at position 4 is backbone-N-
      METHLATION of the Tyrosine
<220> FEATURE:
<221> NAME/KEY: MISC_FEATURE
<222> LOCATION: (10)..(10)
<223> OTHER INFORMATION: Amino acid at position 10 is in the
      D-configuration

<400> SEQUENCE: 31

Lys Arg Phe Tyr Val Val Met Trp Lys Lys
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Amino acid at position 1 is in the
      D-configuration
<220> FEATURE:
<221> NAME/KEY: MISC_FEATURE
<222> LOCATION: (3)..(3)
<223> OTHER INFORMATION: Amino acid at position 3 is backbone-N-
      METHYLATION of the Phenylalanine
<220> FEATURE:
<221> NAME/KEY: MISC_FEATURE
<222> LOCATION: (10)..(10)
<223> OTHER INFORMATION: Amino acid at position 10 is in the
      D-configuration

<400> SEQUENCE: 32

Lys Arg Phe Tyr Val Val Met Trp Lys Lys
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Amino acid at position 1 is in the
      D-configuration
<220> FEATURE:
<221> NAME/KEY: MISC_FEATURE
<222> LOCATION: (7)..(7)
<223> OTHER INFORMATION: Amino acid at position 7 is backbone-N-
      METHYLATION of the Methionine
<220> FEATURE:
<221> NAME/KEY: MISC_FEATURE
<222> LOCATION: (10)..(10)
<223> OTHER INFORMATION: Amino acid at position 10 is in the
      D-configuration
```

<400> SEQUENCE: 33

Lys Arg Phe Tyr Val Val Met Trp Lys Lys
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Amino acid at position 1 is in the
      D-configuration
<220> FEATURE:
<221> NAME/KEY: MISC_FEATURE
<222> LOCATION: (10)..(10)
<223> OTHER INFORMATION: Amino acid at position 10 is in the
      D-configuration

<400> SEQUENCE: 34

Lys Arg Ala Tyr Val Val Met Trp Lys Lys
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Amino acid at position 1 is in the
      D-configuration
<220> FEATURE:
<221> NAME/KEY: MISC_FEATURE
<222> LOCATION: (10)..(10)
<223> OTHER INFORMATION: Amino acid at position 10 is in the
      D-configuration

<400> SEQUENCE: 35

Lys Arg Phe Ala Val Val Met Trp Lys Lys
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Amino acid at position 1 is in the
      D-configuration
<220> FEATURE:
<221> NAME/KEY: MISC_FEATURE
<222> LOCATION: (10)..(10)
<223> OTHER INFORMATION: Amino acid at position 10 is in the
      D-configuration

<400> SEQUENCE: 36

Lys Arg Phe Tyr Ala Val Met Trp Lys Lys
1               5                   10

<210> SEQ ID NO 37
<211> LENGTH: 10
<212> TYPE: PRT
<213> ORGANISM: Artificial Sequence -continued

```
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Amino acid at position 1 is in the
      D-configuration
<220> FEATURE:
<221> NAME/KEY: MISC_FEATURE
<222> LOCATION: (10)..(10)
<223> OTHER INFORMATION: Amino acid at position 10 is in the
      D-configuration

<400> SEQUENCE: 37

Lys Arg Phe Tyr Val Ala Met Trp Lys Lys
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Amino acid at position 1 is in the
      D-configuration
<220> FEATURE:
<221> NAME/KEY: MISC_FEATURE
<222> LOCATION: (10)..(10)
<223> OTHER INFORMATION: Amino acid at position 10 is in the
      D-configuration

<400> SEQUENCE: 38

Lys Arg Phe Tyr Val Val Ala Trp Lys Lys
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Amino acid at position 1 is in the
      D-configuration
<220> FEATURE:
<221> NAME/KEY: MISC_FEATURE
<222> LOCATION: (10)..(10)
<223> OTHER INFORMATION: Amino acid at position 10 is in the
      D-configuration

<400> SEQUENCE: 39

Lys Arg Phe Tyr Val Val Met Ala Lys Lys
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Amino acid at position 1 is in the
      D-configuration
```

```
<220> FEATURE:
<221> NAME/KEY: MISC_FEATURE
<222> LOCATION: (10)..(10)
<223> OTHER INFORMATION: Amino acid at position 10 is in the
      D-configuration

<400> SEQUENCE: 40

Lys Arg Phe Tyr Val Val Met Trp Ala Lys
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Amino acid at position 1 is in the
      D-configuration
<220> FEATURE:
<221> NAME/KEY: MISC_FEATURE
<222> LOCATION: (7)..(7)
<223> OTHER INFORMATION: Xaa at position 7 represents Norleucine
<220> FEATURE:
<221> NAME/KEY: MISC_FEATURE
<222> LOCATION: (10)..(10)
<223> OTHER INFORMATION: Amino acid at position 10 is in the
      D-configuration

<400> SEQUENCE: 41

Lys Arg Phe Tyr Val Val Xaa Trp Lys Lys
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Amino acid at position 1 is in the
      D-configuration
<220> FEATURE:
<221> NAME/KEY: MISC_FEATURE
<222> LOCATION: (8)..(8)
<223> OTHER INFORMATION: Amino acid at position 8 is backbone-N-
      METHYLATION of Tryptophane
<220> FEATURE:
<221> NAME/KEY: MISC_FEATURE
<222> LOCATION: (10)..(10)
<223> OTHER INFORMATION: Amino acid at position 10 is in the
      D-configuration

<400> SEQUENCE: 42

Lys Arg Phe Tyr Val Val Met Trp Lys Lys
1               5                   10
```

COMPOUNDS AND PHARMACEUTICAL USE THEREOF IN THE TREATMENT OF CANCER

The present invention relates to a compound or a pharmaceutical salt thereof comprising a hexapeptide sequence of formula (I), its method of synthesis and its use in anticancer therapy.

The invention also relates to a pharmaceutical composition for use in the treatment of cancer comprising at least one soluble peptide according to the invention or at least one nucleic acid coding for the peptides according to the invention or at least one expression vector coding for the peptides according to the invention, or at least one host cell for the provision of the peptides according to the invention and a pharmaceutically acceptable carrier.

INTRODUCTION/BACKGROUND OF THE INVENTION

Cancer is a malignant neoplasm. It is also a broad group of various diseases, all involving unregulated cell growth. In 2007, cancer caused about 13% of all human deaths worldwide (7.9 million). Rates are rising as more people live to an old age and as mass lifestyle changes occur in the developing world.

Particularly, Chronic Lymphocytic Leukemia (CLL) is the most common adult leukemia in the Western countries and is characterized by a progressive accumulation of monoclonal $CD5^+$ B-lymphocytes in the peripheral blood, bone marrow, and secondary lymphoid organs. The resulting congestion leads to the progressive failure of the immune and hematopoietic systems. High-risk hallmarks predictive of CLL progression include the cytogenetic features' mutation/deletion of 17p13 (TP53) and 11q22-q23 (ATM), IGHV unmutated status, high expression of ZAP70, CD38, soluble CD23 increase and the currently studied and not still validated mutations in NOTCH1, MYD88, BIRC3, XPO1, KLHL6, SF3B1, and POT1 genes [Gribben J G, 2010; Lanasa M C, 2010 and Chiorazzi N. et al., 2005]. Patients with dysfunction relevant to ATM and TP53 genes have the poorest prognosis requiring specific aggressive therapy including allogenic stem cell transplantation [Pospisilova N, 2012]. The characteristics of CLL are: (i) Incurable, as all patients will eventually relapse, underscoring a resistance of the disease to current treatment options, (ii) Very heterogeneous disease in terms of response to the—yet non-optimal—existing treatments, (iii) Drug resistance remains a major cause of treatment failure in CLL and its inevitable fate due to the prolonged natural course of the disease and the repeated treatments, creating a relevant social and health problem, (iv) Mainly affects elderly people and is considered a paradigmatic example of most age-related cancers, (v) Robust and specific markers predictive of response to treatment are still lacking, though urgently needed in order to implement risk-adapted, personalized treatment and maximize clinical benefit while minimizing costs.

Even though the direct cause for the development of this malignancy is not fully understood, it is now well demonstrated that CLL represents a perfect example of a human malignancy caused by an imbalance between proliferation and Programmed Cell Death (PCD) [Chiorazzi N, 2007]. Thus, a better understanding of PCD mechanisms regulating the lifespan of the leukemic CLL cells should provide key advances for therapeutic interventions in this leukemia.

PCD is a self-destruction process characterized by stereotyped ultrastructural changes including mitochondrial alterations, condensation of the nucleus and cytoplasm, membrane blebbing and external display of phosphatidylserine. Intense research performed in the last decade has identified a multitude of enzymes and other regulatory proteins involved in the modulation of PCD. These studies conclude that, in most cases, PCD occurs when a family of cysteine proteases, known as caspases, is activated. Since the induction of apoptosis through the use of caspase activators may theoretically constitute a treatment for cancer, the initial pro-apoptotic anti-cancer trials have focused on caspase activity. Unfortunately, most of these studies are still in preclinical development because of their low efficacy. In part, this may be due to the fact that PCD can proceed even when the caspase cascade is blocked. This fact has revealed the existence of an alternative pathway defined as caspase-independent. A comprehensive analysis of caspase-independent PCD pathways offers therefore a new challenge in the design of therapeutic strategies against CLL and other neoplastic diseases.

As indicated above, drug resistance remains a major cause of treatment failure in CLL. In fact, current therapies are responsible for several side effects, increasing the occurrence of treatment-related disabilities that may ultimately affect the well-being, if not the survival rate, of most patients. Until now, the goal of therapy has been to maintain the best quality of life and start treatment only when patients became symptomatic from their disease. For the majority of patients this means following a "wait-and-see" approach to determine the rate of progression of the disease and assess the development of symptoms. Initial treatments for CLL patients have included either a nucleosid analog (Fludarabine) or an alkylating agent (Chlorambucil). This initial approach has been improved by combination regimens such as fludarabine and cyclophosphamide (FC), or more recently by the addition of rituximab to FC (FCR treatment) that is now accepted as the standard front-line therapy. Alternative treatments have been developed for resistant patients or in relapse such as bendamustine, proteasome inhibitors, or monoclonal antibodies (anti-CD52, optimized anti-CD20, anti-CD23, etc.).

Concerning the current clinical trials, the more relevant are the use of monoclonal antibodies (GA101, lumiliximab, lucatumumab), BH3 mimetics (obatoclax, ABT-263), cyclin-dependent kinase inhibitors (flavopiridol, SNS-032), Lyn-kinase inhibitors (dasatinib, bafetinib), hypomethylating agents (azacytidine, decitabine), histone deacetylase inhibitors (parobinastat), purine analogs (8-chloroadenosine, forodesine), and small modular immunopharmaceuticals (TRU-016). Molecules inhibiting downstream signaling after B-cell receptor ligation are novel oral agents interacting at different targets including phosphatidylinositol 3-kinase inhibitors (CAL-101), Bruton's tyrosine kinase (BTK) (PCI-32765), and Spleen Tyrosine Kinase (SYK)-inhibitors (fostamitinib).

Most of the above-described chemotherapeutic treatments induce cytotoxicity via a caspase-dependent mechanism (see above, page 2) with a quite variable outcome, with many patients having a positive reaction whereas others remain refractory (15-25% of CLL patients become refractory during the course of the disease). Indeed, as leukemic B cells present molecular defects that make them particularly resistant to the caspase-dependent PCD pathway (p53 inactivation, overexpression of anti-apoptotic proteins, such as Mcl-1 or Bcl-2), a significant group of CLL patients are refractory to the current chemotherapeutic treatments. For that reason, the introduction of new drugs that induce PCD via alternative caspase-independent PCD pathways could provide new means of improving the current therapeutic strategies used in CLL treatment.

The CD47 receptor is a widely expressed member of the immunoglobulin (Ig) superfamily, functioning both as a receptor for thrombospondin-1 (TSP-1) and as a ligand for the transmembrane signal regulatory proteins SIRP α and γ [Brown E J et al., 2001]. These molecules regulate various biological phenomena in the immune system, including platelet activation, leukocyte migration, macrophage multinucleation, and PCD. Neither SIRP α nor SIRP γ has been implicated in CD47-induced PCD in contrast to TSP-1, which has been shown to bind CD47 specifically via its COOH-terminal cell-binding domain. Many cancers appear to upregulate CD47 as a mechanism of immune evasion and some relatively recent work showed that CD47 is a prognostic factor and a potential therapeutic target in different types of Non-Hodgkin Lymphomas (NHL), including CLL [Edris, B et al., 2012; Willingham, S. B et al., 2012; Chao, M. P et al., 2010; Jaiswal, S et al., 2009 and Chao, M. P et al., 2011]. It has quite recently been demonstrated that CD47 ligation, by an immobilized anti-CD47 mAb (not by a soluble anti-CD47), induces caspase-independent PCD, even in CLL cells from refractory patients [Mateo V et al., 1999; Roue G et al., 2003; Barbier S et al., 2009; Merle-Beral H et al, 2009; Bras M et al, 2007; Mateo V et al, 2002].

In WO 2013/182650 it was demonstrated that CD47 ligation by 4N1K, a soluble and monovalent decapeptide that mimics the C-terminal domain of TSP-1, induces caspase-independent PCD in B-chronic lymphocytic leukemia (CLL) primary cells. It was demonstrated that, contrary to the anti-CD47 mAb which needs to be immobilized to induced PCD, the soluble 4N1K peptide does not need to be coated on plastic to induce caspase-independent PCD. It was found that a negative control peptide 4NGG (4N1K mutated in two amino acids) is unable to induce PCD, signifying the specificity of the 4N1K PCD induction. Moreover, It was discovered that CD47 ligation by 4N1K and its derivative PKHB1 specifically eliminates leukemic B-cells, and not healthy B-lymphocytes or resting normal B-cells from CLL patients (FIGS. 2, 5 and 6) and thus represents a better means of inducing death than caspase-dependent PCD (this form of death is effective even in CLL cells from drug refractory individuals bearing deletion on 17p13 or I lq22-q23: ATM/TP53 inactivated). In vivo mouse studies fully confirmed the specificity of this peptide strategy in inducing PCD in leukemic cells. Therefore, this invention related to a soluble peptide comprising the amino acids sequence: KRFYVVMWK or a function-conservative variant thereof for use in the treatment of cancer.

However, and although WO 2013/182650 enabled to identify specific peptide sequences for use in the treatment of cancer, there is still a need to identify more potent compounds which present CD47 ligation properties, in particular for cancer research and treatment. The present invention answers this first need by the identification of the pharmacophores residues in a peptide sequence of six essential amino acid residues.

Moreover on a practical point of view and besides the metabolic stability, the use of peptides as therapeutic tools preferably requires the design of compounds stable in liquid formulation, especially in aqueous solutions. This enables an easy preparation of the solution to be injected, should it be prepared extemporaneously. This also enables an easier and cheaper preparation process in comparison with lyophilized products i.e. in the form of powders or more generally as solids, wherein the production costs are high, since this comprises the costs for freezing, producing vacuum and stocking/recycling solvents from the treatment of relatively large quantities of solutions to be dried. Furthermore, in the case of injectable solutions which need to be prepared extemporaneously from a powder and sterile water, the storage, logistics and transport means are more voluminous, heavy (different packaging for different products), complicated, and thus more expensive to deal with.

Therefore, the stability of drugs comprising a peptide sequence in liquid formulations (e.g. aqueous) is an important factor to be considered in peptide drug design and development. Surprisingly, the present inventors have found that the initially designed 4N1K analogues were sometimes prompt to aggregation and they have solved this major problem by the design of new compounds (especially PKT16) described hereunder.

SUMMARY OF THE INVENTION

The present invention generally concerns a compound or a pharmaceutical acceptable salt thereof comprising a hexapeptide sequence of formula (I):

$$-X_1-X_2-X_3-X_4-X_5-X_6- \quad (I)$$

wherein:
$X_1$, $X_2$, $X_3$, $X_4$, $X_5$, $X_6$ are independently linked to each other according to formula (I) via peptide bonds or at least one pseudopeptide bond;

$X_1$ is a residue chosen in the list consisting of substituted or unsubstituted phenylalanine, substituted or unsubstituted para-tyrosine, substituted or unsubstituted ortho-tyrosine, substituted or unsubstituted meta-tyrosine, or substituted or unsubstituted homo-phenylalanine;

$X_2$ is a residue chosen in the list consisting of substituted or unsubstituted para-tyrosine, substituted or unsubstituted ortho-tyrosine, substituted or unsubstituted meta-tyrosine, substituted or unsubstituted phenylalanine, homo-phenylalanine, homo-meta-tyrosine, homo-para-tyro sine or homo-ortho-tyrosine $X_3$ is a residue chosen in the list consisting of substituted or unsubstituted valine, substituted or unsubstituted alanine, substituted or unsubstituted leucine, substituted or unsubstituted isoleucine, preferably valine;

$X_4$ is a residue chosen in the list consisting of substituted or unsubstituted valine, substituted or unsubstituted alanine, substituted or unsubstituted leucine, substituted or unsubstituted isoleucine, preferably valine;

$X_5$ is a residue chosen in the list consisting of substituted or unsubstituted methionine or any amino acid with similar properties such as a methylated homo-cysteine, lysine, norleucine, leucine or isoleucine;

$X_6$ is a residue chosen in the list consisting of substituted or unsubstituted tryptophan, substituted or unsubstituted hetero-tryptophan, substituted or unsubstituted para-tyrosine, substituted or unsubstituted ortho-tyrosine, substituted or unsubstituted meta-tyrosine, substituted or unsubstituted phenylalanine, or substituted or unsubstituted naphthyl-alanine;

$X_1$ is the N-terminal side of the molecule of formula (I), $X_6$ is the C-terminal side of the molecule of formula (I);

the hexapeptide sequence of formula (I) comprises at least one substituted or unsubstituted para-tyrosine, substituted or unsubstituted ortho-tyrosine, substituted or unsubstituted meta-tyrosine residue, characterized in that said compound is an agonist of CD47, with the proviso that said compound is not one disclosed in WO2013/182650 or in WO2015/086727 (which discloses the same peptide structures as WO 2013/182650). Indeed, the present invention has enabled to better understand what in the compounds disclosed in WO2013/182650 enables to improve the activity, in particular on CD47. There are several ways to achieve this. This has also led to realize that the compounds disclosed and claimed in WO2013/182650 are only a minority of compounds which are susceptible to present the activity.

The subject matter of the present invention also concerns a method to produce a compound or a pharmaceutical salt as presently defined characterized in that said method comprises the following successive steps:
a) the hexapeptide (I) is first produced, such as on a solid support via solid support peptide synthesis starting from the C-terminal extremity, with the convenient protecting groups on the amino acid residues $X_1$, $X_2$, $X_3$, $X_4$, $X_5$, $X_6$ side chains;
b) optionally the N-terminal extremity of the hexapeptide (I) is then deprotected and grafted with the convenient fragment;
c) optionally the C-terminal extremity of the hexapeptide (I) is then deprotected or cleaved and grafted with the convenient fragment; and
d) the remaining protecting groups of the hexapeptide (I) are then removed.

Moreover, the subject matter of the present invention concerns a compound or a pharmaceutical acceptable salt as presently defined for its use as a medicament.

Furthermore, the subject matter of the present invention concerns as compound or a pharmaceutical acceptable salt according as presently defined for its use as a CD47 inhibitor, in particular in the treatment of cancer.

The subject matter of the present invention also relates to the use of a hexapeptide sequence of formula (I) as defined presently to provide a CD47 regulating effect to a compound. Indeed, the present invention enables to provide an active CD47 peptide sequence which can be incorporated in another structure (preferably a peptide) to provide this activity. The global activity of the molecule/structure/peptide thus may be an inhibition or a regulation of CD47.

DEFINITIONS

Without being bound to the here-under definition, the expression "with the proviso that said compound is not one disclosed in WO2013/182650" means that any compound per see which has been expressly disclosed in WO 2013/182650 is to be excluded from the scope of the present invention. Therefore the subject matter of the present invention concerns a compound or a pharmaceutical acceptable salt thereof comprising a hexapeptide sequence of formula (I) as defined presently, with the proviso that none of the following peptides are covered:

KRFYGGMWKK;

(D)KRFYGGMW(D)K

KRFYVVMWKK (D)R-F-Y-V-V-M-W-K

R-(D)F-Y-V-V-M-W-K

R-F-(D)Y-V-V-M-W-K

R-F-Y-(D)V-V-M-W-K

R-F-Y-V-(D)V-M-W-K

R-F-Y-V-V-(D)M-W-K

R-F-Y-V-V-M-(D)W-K

R-F-Y-V-V-M-W-(D)K (D)R-(D)F-(D)Y-(D)V-(D)V-(D)M-(D)W-(D)K (D)K-(D)W-(D)M-(D)V-(D)V-(D)Y-(D)F-(D)R

Azido(D)K-(D)W-(D)M-(D)V-(D)V-(D)Y-(D)F-(D)R (D)K-R-F-Y-V-V-M-W-K-K

K-(D)R-F-Y-V-V-M-W-K-K

K-R-(D)F-Y-V-V-M-W-K-K

K-R-F-(D)Y-V-V-M-W-K-K

K-R-F-Y-(D)V-V-M-W-K-K

K-R-F-Y-V-(D)V-M-W-K-K

K-R-F-Y-V-V-(D)M-W-K-K

K-R-F-Y-V-V-M-(D)W-K-K

R-R-F-Y-V-V-M-W-(D)K-K

K-R-F-Y-V-V-M-W-K-(D)K

K-R-F-Y-V-V-M-W-K-(D)R (D)K-R-F-Y-V-V-M-W-K-(D)K (D)K-(D)R-(D)F-(D)Y-(D)V-(D)V-(D)M-(D)W-(D)K-(D)K (D)K-(D)K-(D)W-(D)M-(D)V-(D)V-(D)Y-(D)F-(D)R-(D)K

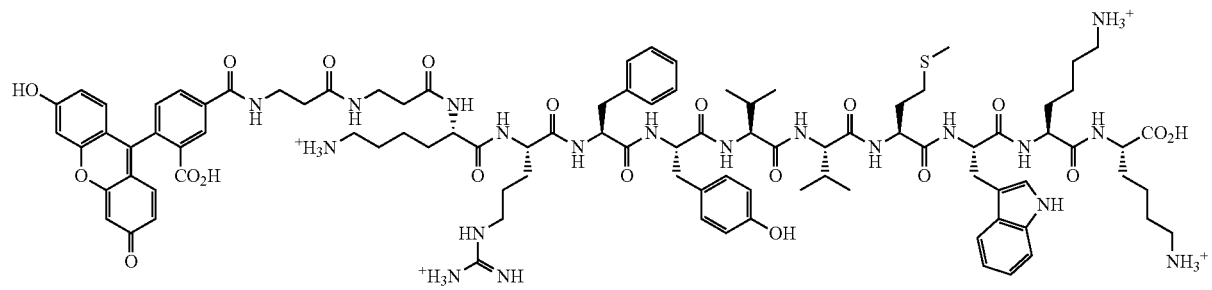

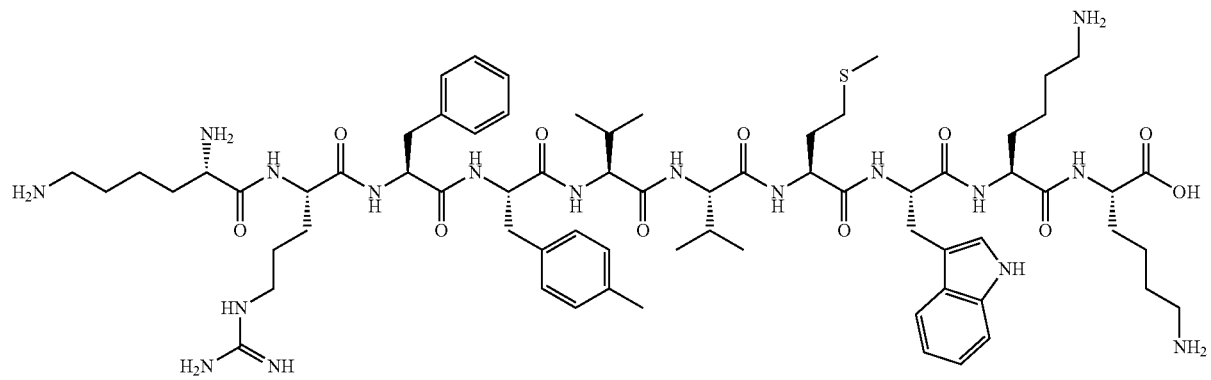
4N1K
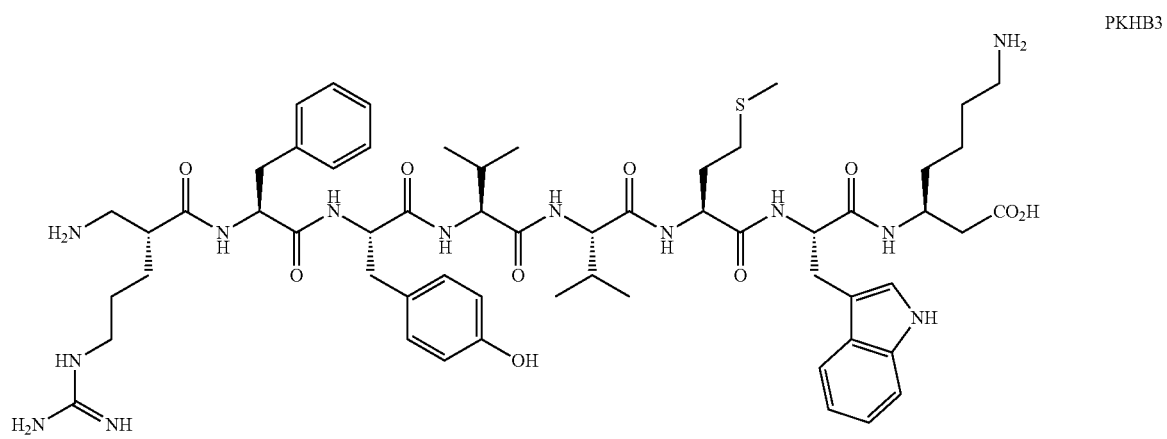
PKHB3
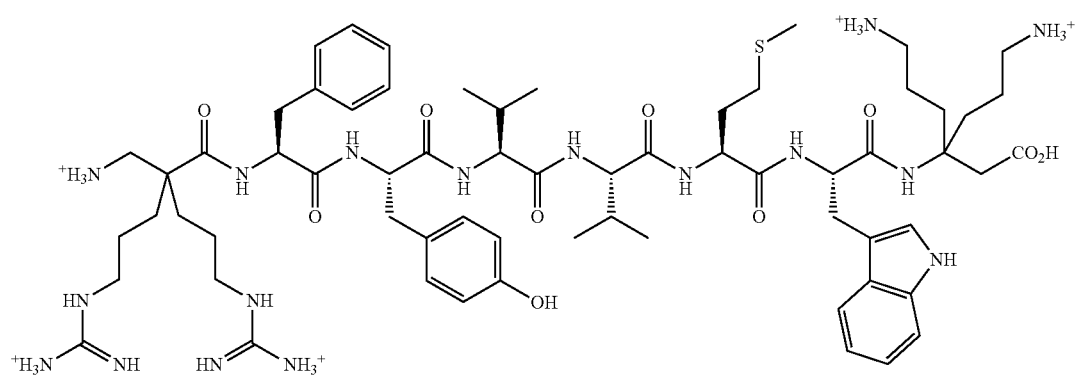
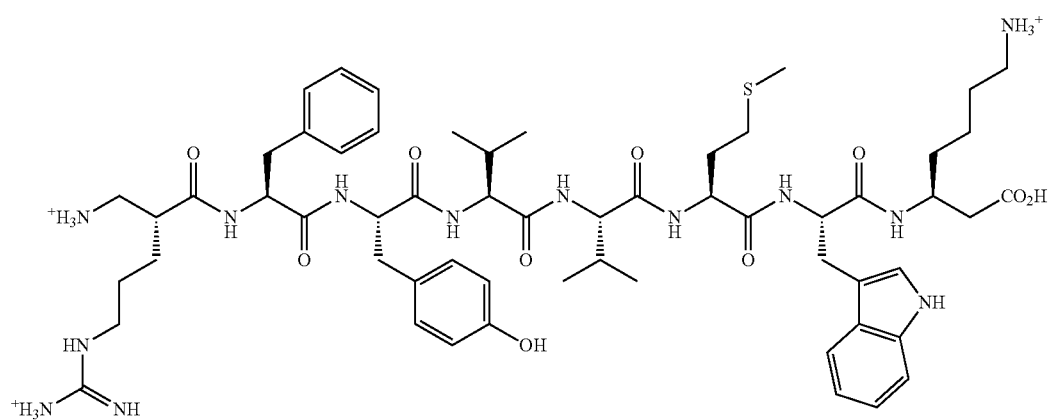

-continued
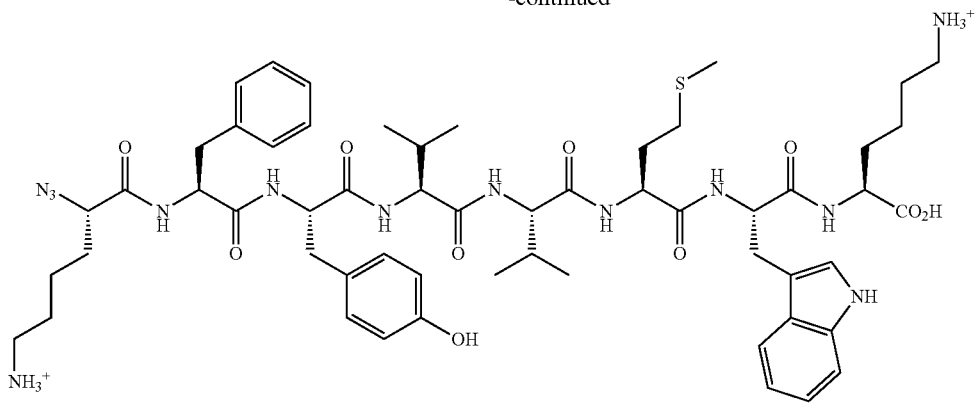
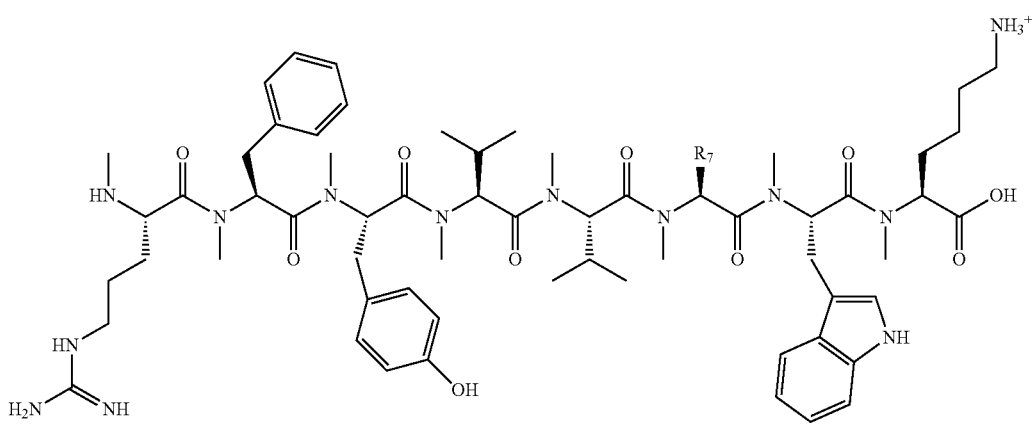
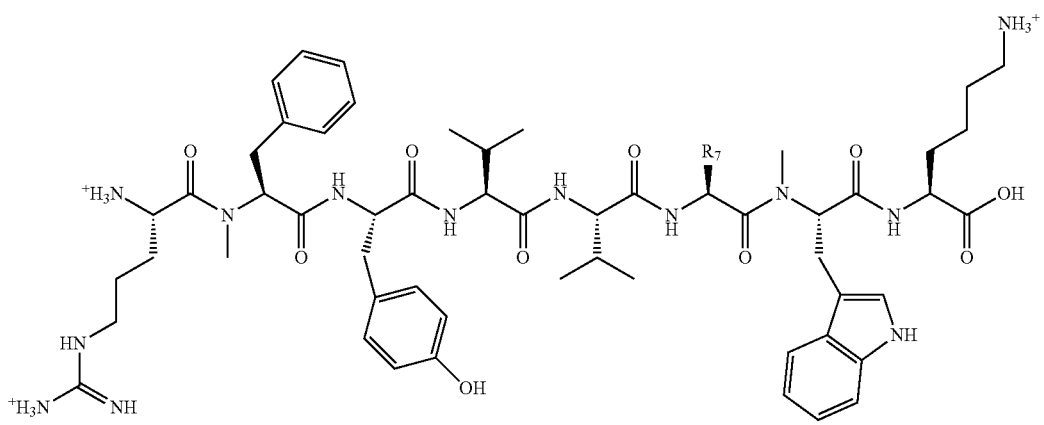
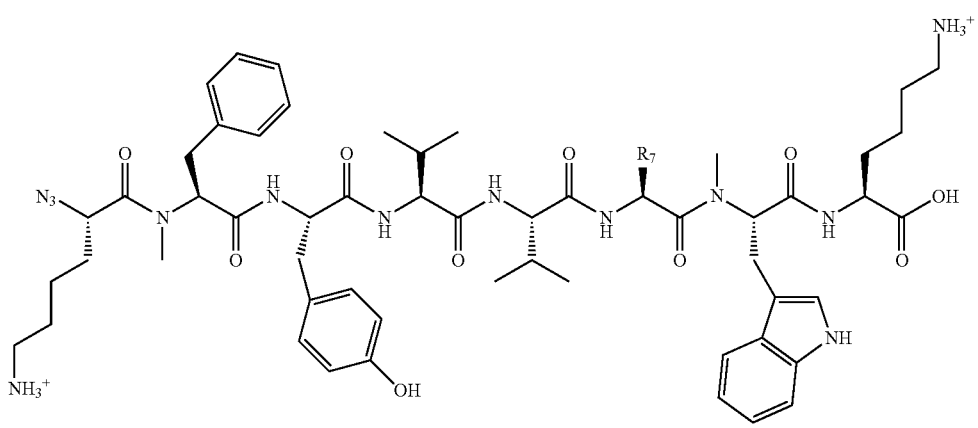

wherein R₇ refers to methionine, methionine sulfoxide, methionine sulfone or alanine or butylglycine or lysine side chains,
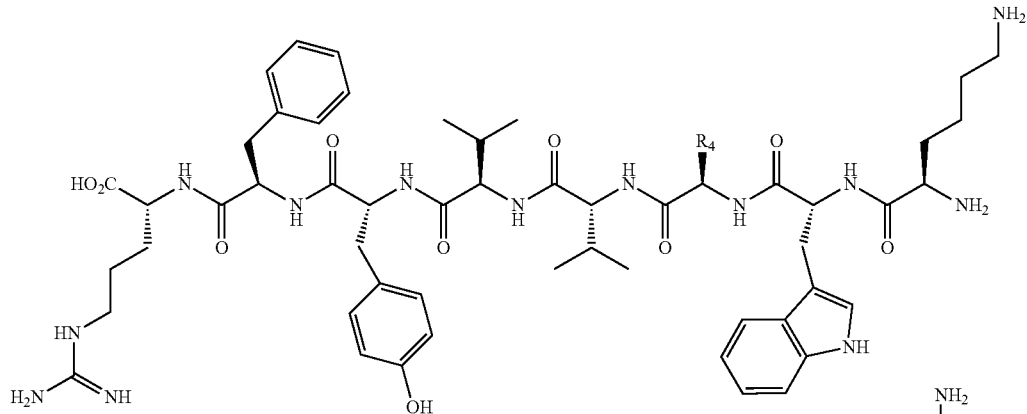
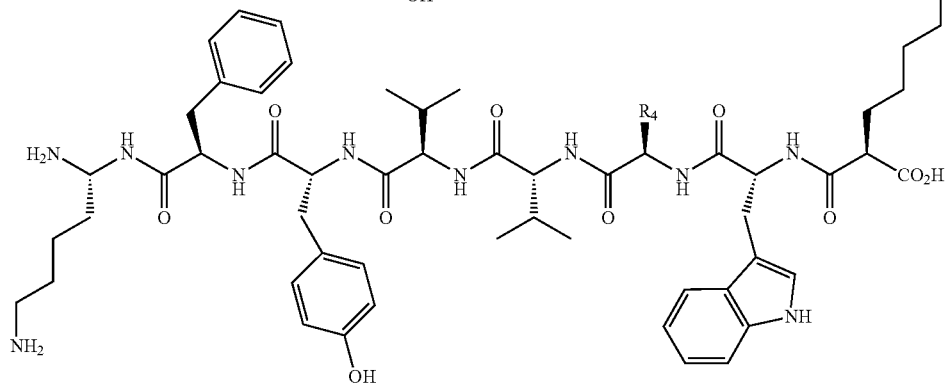
wherein R₄ refers to methionine or alanine or butylglycine or lysine side chains;
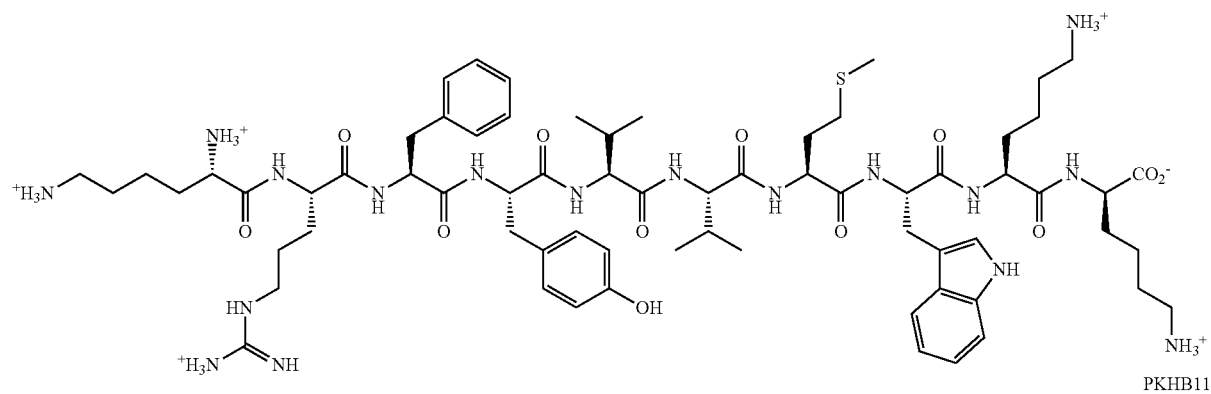
PKHB11
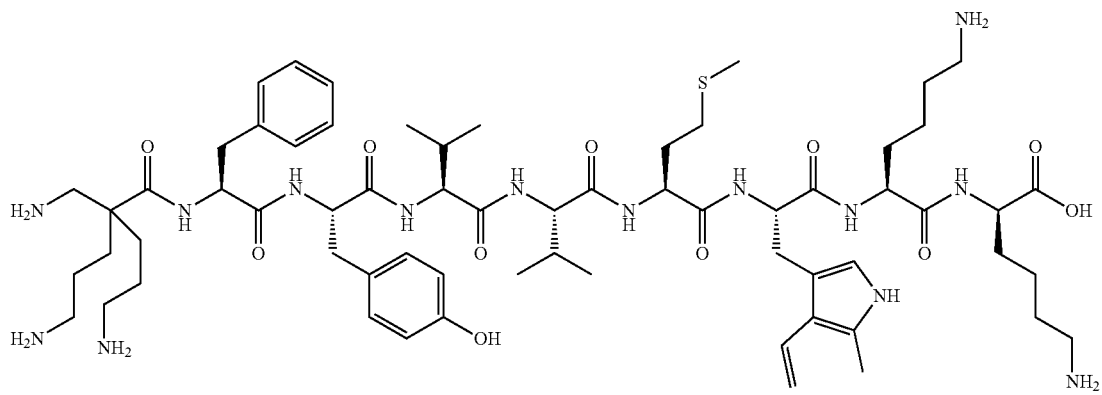

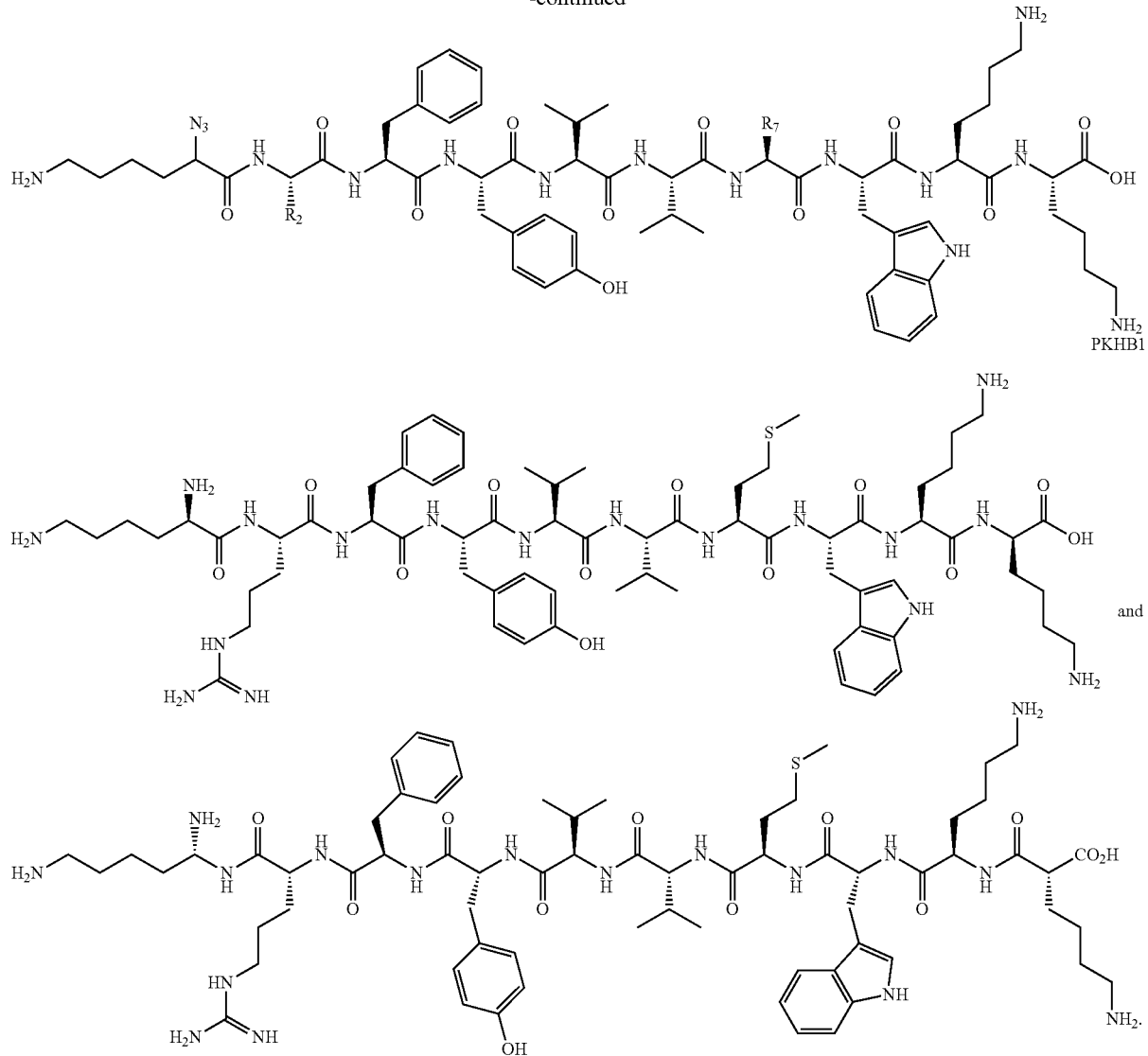
PKHB1
and
Although, the following structures distinguish themselves from the formula (I) of the present invention by a proline in position X4 for PKHB9 and a methyl-proline in position X3 for PKHB10, it is thus obvious that formula (I) does not cover PKHB9 or PKHB10:
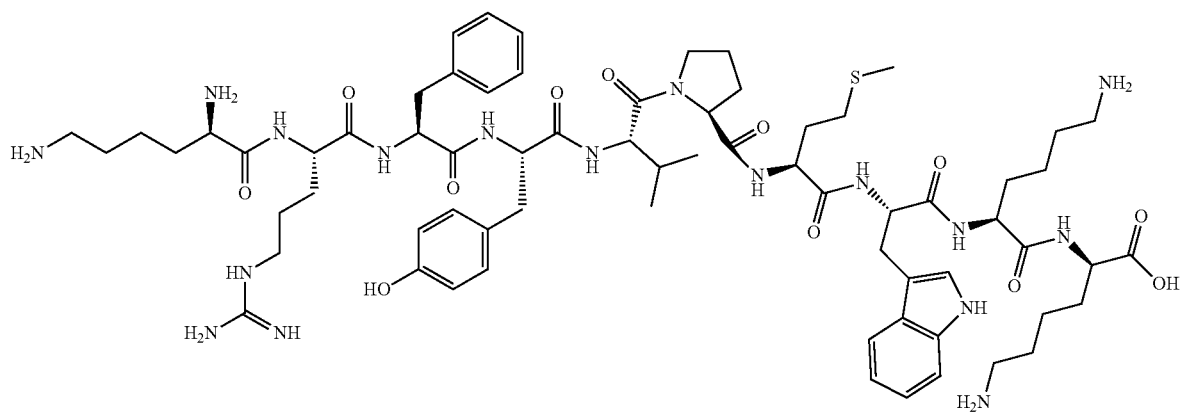
PKHB9

PKHB10

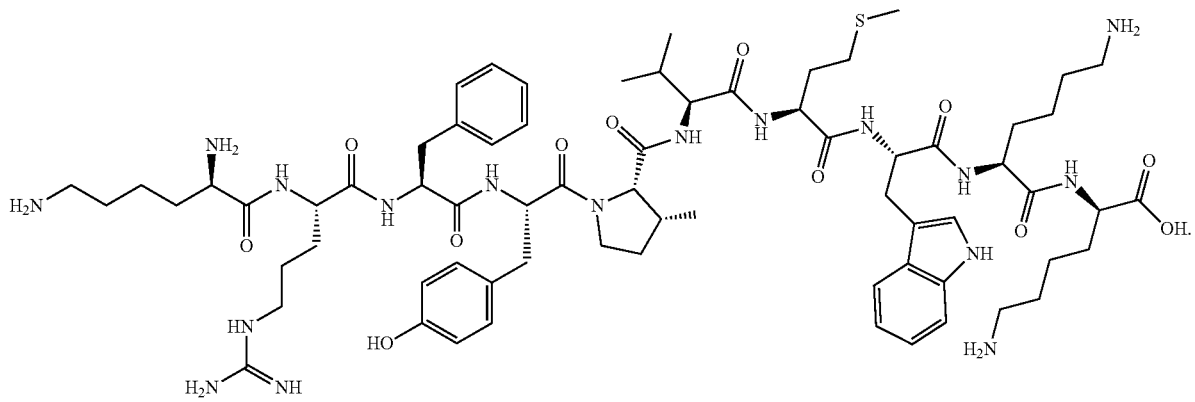

In the same way, formula (I) does not comprise molecules as found on page 14, lines 10 to 13 of WO2015/086727:

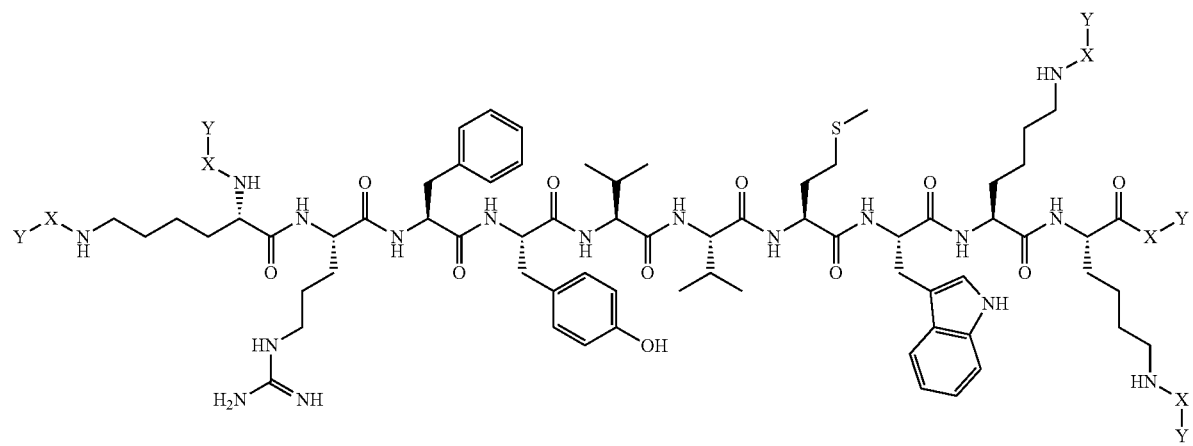

Where X and/or Y can be nothing or hydrogen and/or spacers and/or fluorescentdyes.

Preferably, formula (I) of the present invention does not comprise spacers (as defined in WO2015/086727) or fluorescent dyes (as defined in WO2015/086727). More preferably, formula (I) of the present invention does not comprise any lysine amino acid-residue linked to on or several spacers (as defined in WO2015/086727) or fluorescent dyes (as defined in WO2015/086727).

More precisely, the subject-matter of the present invention concerns a compound or a pharmaceutical acceptable salt thereof comprising a hexapeptide sequence of formula (I) as defined presently, with the proviso that when $X_1$, $X_2$, $X_3$, $X_4$, $X_5$, $X_6$ are all linked to each other according to formula (I) via peptide bonds only:

if $X_5$ is a lysine or a n-butyl-α-glycine, then the hexapeptide (I), with $X_1$, $X_2$, $X_3$, $X_4$ and $X_5$ all except for one being of the (L) configuration, cannot be linked via peptide bonds via $X_1$ to H-(L)Lys- and via $X_6$ to -(L)Lys-OH; or $X_5$ is not a methionine residue in the cases where:

the hexapeptide (I), with $X_1$, $X_2$, $X_3$, $X_4$ and $X_5$ all being of the (L) configuration, is linked via peptide bonds via $X_1$ to the Arg of the dipeptide H-(L)Lys(L)Arg- and via $X_6$ to the dipeptide -(L)Lys(L)Lys-OH;

the hexapeptide (I), with $X_1$, $X_2$, $X_3$, $X_4$ and $X_5$ all being of the (L) configuration, is linked via peptide bonds via $X_1$ to the Arg of the dipeptide [Marker]-(L)Lys(L)Arg- and via $X_6$ to the dipeptide -(L)Lys(L)Lys-OH, wherein the [Marker] is:

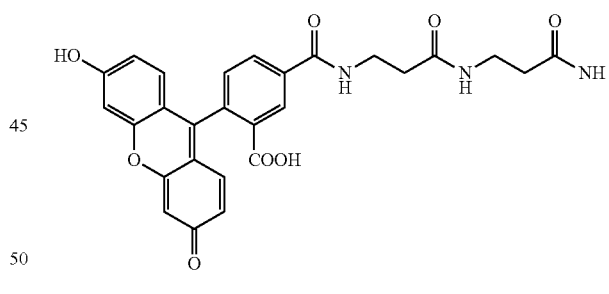

[Marker]

linked by its end of strand NH;

the hexapeptide (I), with $X_1$, $X_2$, $X_3$, $X_4$ and $X_5$ all being of the (L) configuration, is linked via peptide bonds via $X_1$ to the Arg of the dipeptide H-(D)Lys(L)Arg- and via $X_6$ to -(D)Lys-OH;

the hexapeptide (I), with $X_1$, $X_2$, $X_3$, $X_4$ and $X_5$ all being of the (L) configuration, is linked via peptide bonds via $X_1$ to the Arg of the dipeptide H-(L)Lys(L)Arg- and via $X_6$ to the dipeptide -(L)Lys(D)Lys-OH;

the hexapeptide (I), with $X_1$, $X_2$, $X_3$, $X_4$ and $X_5$ all being of the (L) configuration, is linked via peptide bonds via $X_1$ to the Arg of the dipeptide H-(D)Lys(L)Arg- and via $X_6$ to the dipeptide -(L)Lys(L)Lys-OH;

the hexapeptide (I), with $X_1$, $X_2$, $X_3$, $X_4$ and $X_5$ all being of the (L) configuration, is linked via peptide bonds via $X_1$ to the Arg of the dipeptide H-(L)Lys(D)Arg- and via $X_6$ to the dipeptide -(L)Lys(L)Lys-OH;

the hexapeptide (I), with $X_1$, $X_2$, $X_3$, $X_4$ and $X_5$ all except for one being of the (L) configuration, is linked via peptide bonds via $X_1$ to the Arg of the dipeptide H-(L)Lys(L)Arg- and via $X_6$ to the dipeptide -(L)Lys(L)Lys-OH;

the hexapeptide (I), with $X_1$, $X_2$, $X_3$, $X_4$ and $X_5$ all being of the (L) configuration, is linked via peptide bonds via $X_1$ to the Arg of the dipeptide H-(L)Lys(L)Arg- and via $X_6$ to the dipeptide -(D)Lys(L)Lys-OH;

the hexapeptide (I), with $X_1$, $X_2$, $X_3$, $X_4$ and $X_5$ all being of the (L) configuration, is linked via peptide bonds via $X_1$ to the Arg of the dipeptide H-(L)Lys(L)Arg- and via $X_6$ to the dipeptide -(L)Lys(D)Lys-OH;

the hexapeptide (I), with $X_1$, $X_2$, $X_3$, $X_4$ and $X_5$ all being of the (L) configuration, is linked via peptide bonds via $X_1$ to the Arg of the dipeptide H-(D)Lys(L)Arg- and via $X_6$ to the dipeptide -(L)Lys(D)Lys-OH;

the hexapeptide (I), with $X_1$, $X_2$, $X_3$, $X_4$ and $X_5$ all being of the (D) configuration, is linked via peptide bonds via $X_1$ to the Arg of the dipeptide H-(D)Lys(D)Arg- and via $X_6$ to the dipeptide -(D)Lys(D)Lys-OH;

the hexapeptide (I), with $X_1$, $X_2$, $X_3$, $X_4$ and $X_5$ all being of the (L) configuration, is linked via peptide bonds via $X_1$ to the Arg of the dipeptide H-(L)Lys(L)Arg- and via $X_6$ to the Lys of the dipeptide -(L)Lys(D)Arg-OH;

the hexapeptide (I), with $X_1$, $X_2$, $X_3$, $X_4$ and $X_5$ all being of the (L) configuration, is linked via peptide bonds via $X_1$ to the Arg of the dipeptide N-(L)ψ($N_2$)Lys(L)Arg- and via $X_6$ to -(L)Lys-OH;

the hexapeptide (I), with $X_1$, $X_2$, $X_3$, $X_4$ and $X_5$ all being of the (L) configuration, is linked via peptide bonds via $X_1$ to N-(L)ψ($N_2$)Lys- and via $X_6$ to -(L)Lys-OH;

the hexapeptide (I), with $X_1$, $X_2$, $X_3$, $X_4$ and $X_5$ all being of the (L) configuration, is linked via peptide bonds via $X_1$ to H-[beta(2,2)-homo-Lys]- and via $X_6$ to the (L)-Lys of the dipeptide -(L)Lys(D)Lys-OH;

the hexapeptide (I), with $X_1$, $X_2$, $X_3$, $X_4$ and $X_5$ all being of the (L) configuration, is linked via peptide bonds via $X_1$ to H-(L)Arg- or H-(D)Arg- and via $X_6$ to -(L)Lys-OH;

the hexapeptide (I), with $X_1$, $X_2$, $X_3$, $X_4$ and $X_5$ all being of the (L) configuration, is linked via peptide bonds via $X_1$ to H-(L)[homo-Arg]- and via $X_6$ to -(L)Lys-OH;

the hexapeptide (I), with $X_1$, $X_2$, $X_3$, $X_4$ and $X_5$ all being of the (L) configuration, is linked via peptide bonds via $X_1$ to H-(L)[homo-Arg]- and via $X_6$ to -(L)[homo-Lys]-OH;

the hexapeptide (I), with $X_1$, $X_2$, $X_3$, $X_4$ and $X_5$ all being of the (L) configuration, is linked via peptide bonds via $X_1$ to H-[beta(2,2)-homo-Arg]- and via $X_6$ to -[beta(2,2)-homo-Lys]-OH;

the hexapeptide (I), with $X_1$, $X_2$, $X_3$, $X_4$ and $X_5$ all except for one being of the (L) configuration, is linked via peptide bonds via $X_1$ to H-(D)Arg- and via $X_6$ to -(L)Lys-OH;

the hexapeptide (I), with $X_1$, $X_2$, $X_3$, $X_4$ and $X_5$ all except for one being of the (L) configuration, is linked via peptide bonds via $X_1$ to H-(L)Arg- and via $X_6$ to -(L)Lys-OH;

the hexapeptide (I), with $X_1$, $X_2$, $X_3$, $X_4$ and $X_5$ all except for one being of the (L) configuration, is linked via peptide bonds via $X_1$ to H-(L)Arg- and via $X_6$ to -(D)Lys-OH;

or with the proviso that in said compound or salt thereof are not of the following formula:

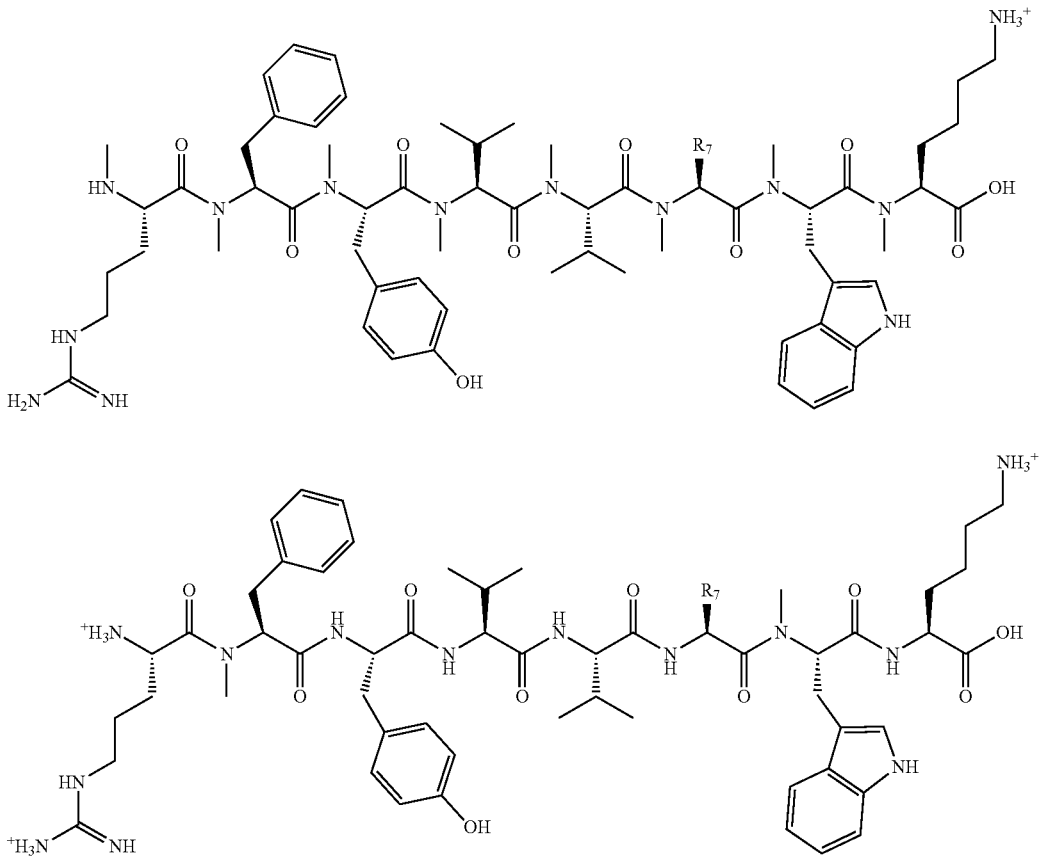

-continued

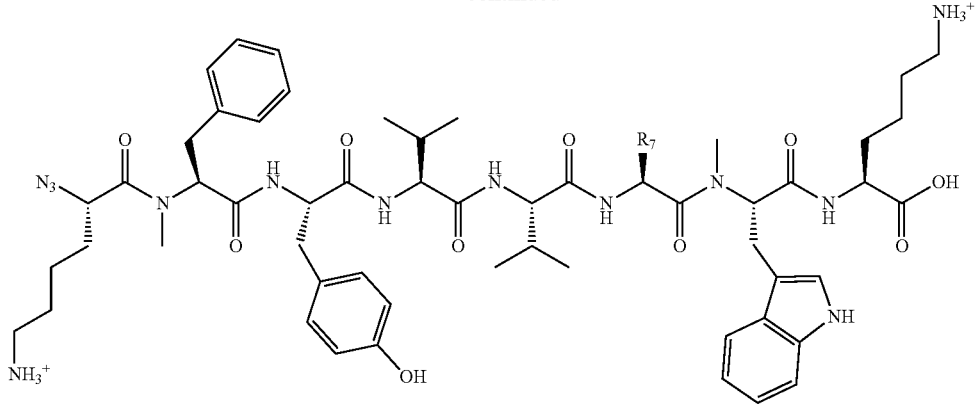

wherein $R_7$ refers to the side chains of methionine, methionine sulfoxide, methionine sulfone, alanine, butylglycine or lysine.

The term "peptide" should be understood to mean a polymer of amino acids, to said amino acids being linked together by a peptide and/or pseudopeptide bond. A peptide generally contains between 2 and 80 to 100 amino acids, the upper limit not being clearly defined. The compounds of the present invention contain peptides between 6 and 80 amino acids, more preferably between 7 and 40 amino acids, and even more preferably between 8 and 20 amino acids.

By "linear peptide" is meant that all the amino acids of the peptide are linked in their sequential order and that the peptide has an N-terminus and a C-terminus.

Generally, by "cyclic peptide" is meant an amino acid sequence without an N-terminus or C-terminus. In the context of the present invention, a cyclic peptide can be linked by a side chain to the solid support, and so the general definition applies, or it can be linked to the support by one of its N-terminal or C-terminal ends and then the ring is closed by means of at least one amino acid side chain.

A "pseudopeptide" is a peptide comprising at least one pseudopeptide bond. A "pseudopeptide bond" links two amino acids in a way different from the —CO—NH— bond. One of the two amino acids can thus be non-natural or replaced by a non-amino acid analog having functional groups required for the pseudopeptide bond such as, for example, a diamine or a malonate type diacid. In the context of the present invention, pseudopeptide bonds are advantageously selected from —CO—N($C_1$-$C_6$ alkyl)- such as —CO—N(Me)-, —CO—N(OH)—, —CO—N($C_1$-$C_6$ alkyl substituted by OH)—, —CO—N($NH_2$)—, —CO—$CH_2$—, —CO—CH($C_1$-$C_6$ alkyl)- such as —CO—CH(Me)-, —CO—O—, —CO—S—, —CS—NH—, —CS—N($C_1$-$C_6$ alkyl)- such as —CS—N(Me)-, —CS—N(OH)—, —CS—N($C_1$-$C_6$ alkyl substituted by OH)—, —CS—N($NH_2$)—, —CS—$CH_2$—, —CS—O—, —CS—S—, —CS—(NH—NH)—, —(C=$CH_2$)—NH—, —(C=$CH_2$)—N($C_1$-$C_6$ alkyl)- such as —(C=$CH_2$)—N(Me)-, —(C=$CH_2$)—N(OH)—, —(C=$CH_2$)—N($C_1$-$C_6$ alkyl substituted by OH)—, —(C=$CH_2$)—N($NH_2$)—, —(C=$CH_2$)—$CH_2$—, —(C=$CH_2$)—O—, —(C=$CH_2$)—S—, —(C=$CH_2$)—(NH—NH)—.

The preferred pseudopeptide bonds according to the present invention are —CO—N($C_1$-$C_6$ alkyl)- such as —CO—N(Me)-, —CO—CH($C_1$-$C_6$ alkyl)- such as —CO—CH(Me)-.

When pseudopeptide bonds are formed, the various reactive groups of the amino acids can also be protected. The term "pseudopeptides" thus also comprises compounds having pseudopeptide bonds whose reactive groups, such as those of the side chains, are protected.

These protective groups are groups known to the person skilled in the art. These protective groups and use thereof are described in work such as, for example, Greene, "Protective Groups in Organic Synthesis", Wiley, New York, 2007 4th edition; Harrison et al., "Compendium of Synthetic Organic Methods", Vol. 1 to 8 (J. Wiley & Sons, 1971 to 1996). Moreover, peptide synthesis techniques are described in Paul Lloyd to Williams, Fernando Albericio, Ernest Giralt, "Chemical Approaches to the Synthesis of Peptides and Proteins", CRC Press, 1997 or Houben-Weyl, "Methods of Organic Chemistry, Synthesis of Peptides and Peptidomimetics", Vol. E 22a, Vol. E 22b, Vol. E 22c, Vol. E 22d., M. Goodmann Ed., Georg Thieme Verlag, 2002.

An example of a preferred pseudopeptide is depsipeptides, i.e., peptides in which is at least one peptide bond has been replaced by an ester bond —COO—.

The expression "amino acid" refers to any molecule having at least one carboxylic acid, at least one amine and at least one carbon linking said amine and said carboxylic acid.

Preferably, the amino acids which can be used in the context of the present invention are so-called "natural" amino acids and/or synthetic amino acids as defined below. Preferably, the amino acids of the present invention are L-amino acids.

The expression "natural amino acid" represents, among other things, the following amino acids: glycine (Gly), alanine (Ala), valine (Val), leucine (Leu), isoleucine (Ile), serine (Ser), threonine (Thr), phenylalanine (Phe), tyrosine (Tyr), tryptophan (Trp), cysteine (Cys), methionine (Met), proline (Pro), aspartic acid (Asp), asparagine (Asn), glutamine (Gln), glutamic acid (Glu), histidine (His), arginine (Arg) and lysine (Lys). The preferred natural amino acids according to the present invention are L-amino acids.

By "synthetic amino acid" is meant all non-natural amino acids as defined above. These synthetic amino acids can be selected from: β-alanine, allylglycine, tert-leucine, norleucine (Nle), 3-aminoadipic acid, 2-aminobenzoic acid, 3-aminobenzoic acid, 4-acid, 2-aminobutanoic acid, 4-aminolcarboxymethyl piperidin, 1-amino-1-cyclobutanecarboxylic acid, 4-aminocyclohexaneacetic acid, 1-amino-1-cyclohexanecarboxylic acid, (1R,2R)-2-aminocyclohexanecarboxylic acid, (1R,2S)-2-aminocyclohexanecarboxylic acid, (1S,2R)-2-aminocyclohexanecarboxylic acid, (1S,2S)-2-aminocyclohexanecarboxylic acid, 3-aminocyclohexanecarboxylic acid, 4-aminocyclohexanecarboxylic acid, (1R,2R)-2-aminocyclopentanecarboxylic acid, (1R,2S)-2-aminocyclopentanecarboxylic acid, 1-amino-1-cyclopentanecarboxylic acid, 1-amino-1-cyclopropanecarboxylic acid, 3-aminomethylbenzoic acid, 4-aminomethylbenzoic acid, 2-aminobutanoic acid, 4-aminobutanoic acid, 6-aminohexanoic acid, 1-aminoindane-1-carboxylic acid, 2-aminoisobutyric acid (Aib), 4-aminomethyl-phenylacetic acid, 4-aminophenylacetic acid, 3-amino-2-naphthoic acid, 4-aminophenylbutanoic acid, 4-amino-5-(3-indolyl)-pentanoic acid, (4R,5S)-4-amino-5-methylheptanoic acid, (R)-4-amino-5-methylhexanoic acid, (R)-4-amino-6-methylthiohexanoic acid, (S)-4-amino-pentanoic acid, (R)-4-amino-5-phenylpentanoic acid, 4-aminophenylpropionic acid, (R)-4-aminopimeric acid, (4R,5R)-4-amino-5-hydroxyhexanoic acid, (R)-4-amino-5-hydroxypentanoic acid, (R)-4-amino-5-(p-hydroxyphenyl)-pentanoic acid, 8-aminooctanoic acid, (2S,4R)-4-amino-pyrrolidine-2-carboxylic acid, (2S,4S)-4-amino-pyrrolidine-2-carboxylic acid, azetidine-2-carboxylic acid, (2S,4R)-4-benzyl-pyrrolidine-2-carboxylic acid, (S)-4,8-diaminooctanoic acid, tert-butylglycine, γ-carboxyglutamate, β-cyclohexylalanine, citrulline, 2,3-diamino propionic acid, hippuric acid, homocyclohexylalanine, moleucine, homophenylalanine, 4-hydroxyproline, indoline-2-carboxylic acid, isonipecotic acid, α-methyl-alanine, naphthyl-alanine, nicopetic acid, norvaline, octahydroindole-2-carboxylic acid, ornithine (Orn), penicillamine, phenylglycine (Phg), 4-phenyl-pyrrolidine-2-carboxylic acid, propargylglycine, 3-pyridinylalanine, 4-pyridinylalanine, 1-pyrrolidine-3-carboxylic acid, sarcosine, statins, tetrahydroisoquinoline-1-carboxylic acid, 1,2,3,4-tetrahydroisoquinoline-3-carboxylic acid, tranexamic acid, 4,4-difluoro proline, 4-fluoro proline, alpha-(3,4-difluorobenzyl)-proline, gamma-(3,4-difluorobenzyl)-proline, alpha-(trifluoromethyl)phenylalanine, hexafluoroleucine, 5,5,5-trifluoroleucine, 6,6,6-trifluoronorleucine, 2-(trifluoromethyl)leucine, 2-(trifluoromethyl)norleucine, 4,4,4-trifluorovaline, 4,4,4,4',4',4'-hexafluorovaline, pentafluorophenylalanine, 2,3-difluorophenyl alanine, 2,4-difluorophenylalanine, 2,5-difluorophenylalanine, 2,6-difluorophenyl alanine, 3,4-difluorophenylalanine, 3,5-difluorophenylalanine, 3,3-difluoro-3-(4-fluorophenyl)alanine, 2,3-difluorophenylglycine, 2,4-difluorophenylglycine, 2,5-difluorophenylglycine, 3,4-difluorophenylglycine, 4,4-difluoroethylglycine, 4,4,4-trifluoroethylglycine, 4-fluorotryptophan, 5-fluorotryptophan, 6-fluorotryptophan, 5-methyltryptophan, S-tritylcysteine, selenocysteine, selenomethionine, ethionine, β-(2-thienyl)alanine, β-chloroalanine, thiazolylalanine, triazolalanine, p-fluorophenylalanine, o-fluorophenylalanine, m-fluorophenylalanine, dihydroxyphenylalanine, 2,5-dihydrophenylalanine, thioproline, pipecolic acid, canavanine, indospicine, 3,4-dehydroproline, histidinol and hexafluoronorleucine, and the like.

The term "side chain of an amino acid" refers to the fragment carried by the alpha carbon of an amino acid. For example, the side chains of natural amino acids such as glycine, valine, alanine and aspartic acid correspond to the hydrogen atom and the groups isopropyl, methyl and —CH$_2$—COOH, respectively.

The side chains of other amino acids can be included in the definition of side chain of an amino acid, such as those of the following amino acids: 4-amino tetrahydropyran-4-carboxylic acid, allylglycine, diamino butyric acid, diamino propionic acid, aminoserine, aminobutyric acid, amino butylglycine, phenylglycine, 4-fluorophenylalanine, 4-nitrophenylalanine, citrulline, cyclohexylalanine, thienylalanine, and the like.

Amino acid side chains can be protected by protective groups (P) and more particularly N-protective, O-protective or S-protective groups when these chains contain the corresponding heteroatoms. Certain reactive functional groups of peptides must be protected during the synthesis of said peptides. Indeed, peptides are typically synthesized via activation of the carboxylic acid functional group of an amino acid, or of a chain of amino acids, by means of a coupling agent. This activated acid is brought together with an amino acid, or a chain of amino acids, whose terminal amine is not protected, thus resulting in the formation of an amide bond, also called a peptide bond. The coupling conditions and the coupling agents used are very well-known to the person skilled in the art.

Protective groups (P) are also groups known to the person skilled in the art. These protective groups and use thereof are described in work such as, for example, Greene, "Protective Groups in Organic Synthesis", Wiley, New York, 2007 4th edition; Harrison et al., "Compendium of Synthetic Organic Methods", Vol. 1 to 8 (J. Wiley & Sons, 1971 to 1996). Moreover, peptide synthesis techniques are described in Paul Lloyd-Williams, Fernando Albericio, Ernest Giralt, "Chemical Approaches to the Synthesis of Peptides and Proteins", CRC Press, 1997 or Houben-Weyl, "Methods of Organic Chemistry, Synthesis of Peptides and Peptidomimetics", Vol. E 22a, Vol. E 22b, Vol. E 22c, Vol. E 22d., M. Goodmann Ed., Georg Thieme Verlag, 2002. Protective groups carried by a nitrogen atom will be referred to as N-protective groups.

The same applies to S-protective and O-protective groups, etc. For example, hydroxyl can be protected by a trityl group, or carboxylic acid can be protected in the form of a tert-butyl ester. In the case of synthesis on a solid support, it is the resin which serves as a protective group to the C-terminal carboxylic functional group.

Protection of the amino group (i.e., "alpha amine") of the amino acid can be carried out, for example, by a tert-butyloxycarbonyl group (hereinafter referred to as Boc-) or a -9-fluorenylmethyloxycarbonyl group (hereinafter referred to as Fmoc-).

Protection is carried out according to known methods of the prior art. For m example, protection by the Boc-group can be obtained by reacting the amino acid with di-tert-butylpyrocarbonate (Boc$_2$O). When protecting functional groups of natural amino acids, the amino acids obtained are synthetic until the protective group(s) are removed, thus releasing the so-called natural amino acid.

Peptides are typically synthesized via activation of the carboxylic acid functional group of an amino acid, or a chain of amino acids, by means of a coupling agent. This activated acid is brought together with an amino acid, or a chain of amino acids, whose terminal amine is unprotected, thus resulting in the formation of an amide bond, also called a peptide bond. The coupling conditions and coupling agents used are well-known to the person skilled in the art and are described, for example, in work such as Greene, "Protective Groups in Organic Synthesis", Wiley, New York, 2007 4th edition; Harrison et al., "Compendium of Synthetic Organic Methods", Vol. 1 to 8 (J. Wiley & Sons, 1971 to 1996). Moreover, peptide synthesis techniques are described in Paul Lloyd-Williams, Fernando Albericio, Ernest Giralt, "Chemical Approaches to the Synthesis of Peptides and Proteins", CRC Press, 1997 or Houben-Weyl, "Methods of Organic Chemistry, Synthesis of Peptides and Peptidomimetics", Vol. E 22a, Vol. E 22b, Vol. E 22c, Vol. E 22d., M. Goodmann Ed., Georg Thieme Verlag, 2002.

The peptide bonds "—NH—CO—" (or their equivalent pseudopeptide bonds) embedded in the backbone of the peptide sequence enable to give the peptide a "C-terminal extremity" which corresponds to the far-side CO of the peptide (i.e. the last CO of the sequence), which can be either a COOH, COO—, CONH$_2$, CO— resin, COOtBu, etc. In a similar way the "N-terminal extremity" of the peptide is thus the opposite side of the peptide which can be either a —NH$_2$, —NH$_3^+$, —NH-Boc, —NH-Fmoc, N$_3$, NAc, etc.

The expression "substituted or unsubstituted phenylalanine", means a phenylalanine residue which is substituted on the side chain, i.e. CH$_2$-Ph, by e.g. a halogen atom, preferably fluorine, or a group chosen from —NH$_2$ or —NO$_2$. In a particular embodiment of the present invention, the substitution is on the para position of the phenyl.

The expression "substituted or unsubstituted homo-phenylalanine", means a homo-phenylalanine residue which is substituted on the side chain, i.e. —CH$_2$—CH$_2$-Ph, by e.g. a halogen atom, preferably fluorine, or a group chosen from —NH$_2$, —NO$_2$ or —OH. In a particular embodiment of the present invention, the substitution is on the para position of the phenyl.

Although the term "tyrosine" can embrace para-tyrosine, ortho-tyrosine or meta-tyrosine, it preferably means para-tyrosine.

The expression "substituted or unsubstituted para-tyrosine", means a para-tyrosine residue which is substituted on the side chain, i.e. —CH$_2$-Ph-OH wherein OH is in position 4, by e.g. a halogen atom, preferably fluorine, or a group chosen from amine, nitro, hydroxyl. In a particular embodiment of the present invention, the substitution is either the meta (positions 3 and/or 5) and/or ortho positions (positions 2 and/or 6) of the phenyl.

The expression "substituted or unsubstituted ortho-tyrosine", means a ortho-tyrosine residue which is substituted on the side chain, i.e. —CH$_2$-Ph-OH wherein OH is in position 2, by e.g. a halogen atom, preferably fluorine, or a group chosen from amine, nitro, hydroxyl. In a particular embodiment of the present invention, the substitution is either the meta (positions 3 and/or 5), ortho (position 6) and/or para (position 4) positions of the phenyl.

The expression "substituted or unsubstituted meta-tyrosine", means a meta-tyrosine residue which is substituted on the side chain, i.e. —CH$_2$-Ph-OH wherein OH is in position 3, by e.g. a halogen atom, preferably fluorine, or a group chosen from amine, nitro, hydroxyl. In a particular embodiment of the present invention, the substitution is either the meta (position 5), ortho (positions 2 and/or 6) and/or para (position 4) positions of the phenyl.

The expression "substituted or unsubstituted valine", means a valine residue which is substituted on the side chain, i.e. —CH—(CH$_3$)$_2$, by e.g. a halogen atom, preferably fluorine, or a group chosen from amine, nitro, hydroxyl. In a particular embodiment of the present invention, the substitution is at least one hydrogen atom replaced by a fluorine atom, i.e. the side chain is —CH—[(CH$_3$)(CF$_3$)].

The expression "substituted or unsubstituted alanine", means a alanine residue which is substituted on the side chain, i.e. —CH$_3$, by e.g. a halogen atom, preferably fluorine, or a group chosen from amine, nitro, hydroxyl. In a particular embodiment of the present invention, the substitution is at least one hydrogen atom replaced by a fluorine atom, i.e. the side chain is —CF$_3$.

The expression "substituted or unsubstituted leucine", means a leucine residue which is substituted on the side chain, i.e. —CH$_2$—CH—(CH$_3$)$_2$, by e.g. a halogen atom, preferably fluorine, or a group chosen from amine, nitro, hydroxyl. In a particular embodiment of the present invention, the substitution is at least one hydrogen atom replaced by a fluorine atom, i.e. the side chain is —CH$_2$—CH—[(CH$_3$)(CF$_3$)].

The expression "substituted or unsubstituted isoleucine", means a isoleucine residue which is substituted on the side chain, i.e. —CH—[(CH$_3$)(CH$_2$CH$_3$)], by e.g. a halogen atom, preferably fluorine, or a group chosen from amine, nitro, hydroxyl. In a particular embodiment of the present invention, the substitution is at least one hydrogen atom replaced by a fluorine atom, i.e. the side chain is —CH—[(CF$_3$)(CH$_2$CH$_3$)].

The expression "substituted or unsubstituted methionine", means a methionine residue which is substituted on the side chain, i.e. —CH$_2$—CH$_2$—S—CH$_3$, by e.g. a halogen atom, preferably fluorine, or a group chosen from amine, nitro, hydroxyl. In a particular embodiment of the present invention, the substitution is at least one hydrogen atom replaced by a fluorine atom, i.e. the side chain is —CF$_2$—CH$_2$—S—CH$_3$.

The term "norleucine" means 2-aminohexanoic acid.

The expression "substituted or unsubstituted tryptophan", means a tryptophan residue which is substituted on the side chain, i.e. —CH$_2$-(1H-indol-3-yl), by e.g. a halogen atom, preferably fluorine, or a group chosen from amine, nitro, hydroxyl. In a particular embodiment of the present invention, the substitution is at least one hydrogen atom replaced by a fluorine atom, i.e. the side chain is —CF$_2$-(1H-indol-3-yl).

A "hetero-tryptophan" is a tryptophan amino acid residue wherein the "NH" of the —CH$_2$-(1H-indol-3-yl) side chain has been replaced by an "0" or a "S". The expression "substituted or unsubstituted hetero-tryptophan", means a hetero-tryptophan residue which is substituted on the side chain by e.g. a halogen atom, preferably fluorine, or a group chosen from amine, nitro, hydroxyl. In a particular embodiment of the present invention, the substitution is at least one hydrogen atom replaced by a fluorine atom.

A "naphthyl-alanine" is an alanine amino acid residue substituted by a naphthalene fragment, i.e. the side chain is —CH$_2$-(naphthyl). The expression "substituted or unsubstituted naphthyl-alanine", means a naphthyl-alanine residue which is substituted on the side chain by e.g. a halogen atom, preferably fluorine, or a group chosen from amine, nitro, hydroxyl. In a particular embodiment of the present invention, the substitution is naphthyl fragment.

The expression "agonist of CD47" means that the compound will bind to the CD47 receptor. As explained above, the CD47 receptor is a widely expressed member of the immunoglobulin (Ig) superfamily, functioning both as a receptor for thrombospondin-1 (TSP-1) and as a ligand for the transmembrane signal regulatory proteins SIRP α and γ [Brown E J et al., 2001]. Preferably the dissociation constant (KD) to characterize such agonists is inferior to 50 μM, preferably inferior to 20 μM, more preferably inferior to 15 μM, even more preferably inferior to 10 μM or 5 μM.

Within the framework of the present invention, the expression "$C_1$-$C_6$ alkyl group" means any linear saturated hydrocarbon radical from one to six carbon atoms or branched saturated hydrocarbon radical from three to six carbon atoms. Examples of ($C_1$-$C_6$) alkyl radicals include, but are not limited to, methyl, ethyl, n-propyl, isopropyl, 1-ethylpropyl, sec-butyl, iso-butyl, tert-butyl, n-butyl, n-pentyl, n-hexyl, etc.

Within the framework of the present invention, "$C_1$-$C_6$ linear alkyl group" means any linear saturated hydrocarbon radical having from one to six carbon atoms. Examples of linear $C_1$-$C_6$ alkyl radicals consist in methyl, ethyl, n-propyl, n-butyl, n-pentyl, n-hexyl.

Within the framework of the present invention, "$C_3$-$C_6$ branched alkyl group" means any branched saturated hydrocarbon radical having from three to six carbon atoms. Examples of branched $C_3$-$C_6$ alkyl radicals include, but are not limited to, isopropyl, 1-ethylpropyl, sec-butyl, ter-butyl etc.

Within the framework of the present invention, "$C_5$-$C_8$ aryl group" means an aromatic group such as a phenyl or a pyridinyl group.

Within the framework of the present invention, "$C_1$-$C_6$ alkoxy group" means a $C_1$-$C_6$ alkyl group as defined above linked to the rest of the molecule by an oxygen atom ("O"). Examples of such alkoxy groups are methoxy, ethoxy, n-propyloxy, isopropyloxy, 1-ethylpropyloxy, sec-butyloxy, iso-butyloxy, tert-butyloxy, n-butyloxy, n-pentyloxy, n-hexyloxy, etc.

Within the framework of the present invention, "$C_5$-$C_8$ aryloxy group" means a $C_5$-$C_8$ aryl group as defined above linked to the rest of the molecule by an oxygen atom ("O"). Examples of such aryloxy groups are phenoxy or pyridiniloxy.

Within the framework of the present invention, the term "therapeutically effective amount" is intended for a minimal amount of active agent, which is necessary to impart therapeutic benefit to a subject. For example, a "therapeutically effective amount of the active agent" to a subject is an amount of the active agent that induces, ameliorates or causes an improvement in the pathological symptoms, disease progression, or physical conditions associated with the disease affecting the subject.

Within the framework of the present invention, the term "treating" concerns a disorder or a condition refers to reversing, alleviating or inhibiting the process of one or more symptoms of such disorder or condition.

Within the framework of the present invention, the term "subject" denotes a mammal, such as a rodent, a feline, a canine, and a primate. Preferably a subject according to the invention is a human.

DETAILED DESCRIPTION

The subject matter of the present invention specifically concerns a compound or a pharmaceutical acceptable salt thereof as defined above, characterized in that the Kd value with CD47 is inferior to 50 µM, preferably inferior to 20 µM, more preferably inferior to 15 µM, even more preferably inferior to 10 µM or 5 µM. Indeed, solid phase synthesis of peptides as developed in the last 50 years or-so has enabled to easily produce just about any peptide (or at least the person skilled in the art now knows to what extend this is possible or not), in particular up-to 30 or 20mers, with e.g. automatized peptide synthesizers. Moreover it is relatively easy to test the affinity of molecules on a given target, such as CD47. It is thus well in the reach of the person skilled in the art to simply test one of the peptides covered by formula (I) as presently defined to check whether it presents the desired activity (especially as it is foreseen that most of the peptides covered should have this activity). This CD47 activity feature, although being of prime importance, is a secondary aspect of the present invention which has set the boundaries of the molecules presenting the activity, i.e. the sequence of formula (I) above.

The present invention generally concerns a compound or a pharmaceutical acceptable salt thereof comprising a hexapeptide sequence of formula (I):

$$-X_1-X_2-X_3-X_4-X_5-X_6- \qquad (I)$$

wherein:
$X_1$, $X_2$, $X_3$, $X_4$, $X_5$, $X_6$ are independently linked to each other according to formula (I) via peptide bonds or at least one pseudopeptide bond;

$X_1$ is a residue chosen in the list consisting of substituted or unsubstituted phenylalanine, substituted or unsubstituted para-tyrosine, substituted or unsubstituted ortho-tyrosine, substituted or unsubstituted meta-tyrosine, or substituted or unsubstituted homo-phenylalanine;

$X_2$ is a residue chosen in the list consisting of substituted or unsubstituted para-tyrosine, substituted or unsubstituted ortho-tyrosine, substituted or unsubstituted meta-tyrosine, substituted or unsubstituted phenylalanine, homo-phenylalanine, homo-meta-tyrosine, homo-para-tyro sine or homo-ortho-tyrosine $X_3$ is a residue chosen in the list consisting of substituted or unsubstituted valine, substituted or unsubstituted alanine, substituted or unsubstituted leucine, substituted or unsubstituted isoleucine, preferably valine;

$X_4$ is a residue chosen in the list consisting of substituted or unsubstituted valine, substituted or unsubstituted alanine, substituted or unsubstituted leucine, substituted or unsubstituted isoleucine, preferably valine;

$X_5$ is a residue chosen in the list consisting of substituted or unsubstituted methionine, or any amino acid with similar properties, lysine, norleucine, leucine or isoleucine;

$X_6$ is a residue chosen in the list consisting of substituted or unsubstituted tryptophan, or any amino acid with similar properties, substituted or unsubstituted hetero-tryptophan, substituted or unsubstituted para-tyrosine, substituted or unsubstituted ortho-tyrosine, substituted or unsubstituted meta-tyrosine, substituted or unsubstituted phenylalanine, or substituted or unsubstituted naphthyl-alanine;

$X_1$ is the N-terminal side of the molecule of formula (I), $X_6$ is the C-terminal side of the molecule of formula (I);

comprising at least one substituted or unsubstituted para-tyrosine, substituted or unsubstituted ortho-tyrosine, substituted or unsubstituted meta-tyrosine residue, with the proviso that said compound is not one disclosed in WO2013/182650, more specifically characterized in terms of structure in that:
formula (I) is embedded in a peptide structure comprising in total (i.e. counting the sequence of formula (I)) 6 to 20 amino acids, more preferably 7 to 15 amino acids, yet more preferably 8 to 12 amino acids, most preferably 10 amino acids;

$X_5$ is a lysine, norleucine, leucine or isoleucine, and preferably $X_1$ is a phenylalanine, preferably $X_2$ is a tyrosine, preferably $X_3$ is a valine, preferably $X_4$ is a valine and preferably $X_6$ is a tryptophan;

the at least one pseudopeptide bond is an N-methyl peptide bond, preferably on the N-terminal or C-terminal side of formula (I) (i.e. comprised in a fragment/fragments linked to $X_1$ and/or $X_6$); and/or $X_2$ the ionic partial charge on either the C-terminal and/or the N-terminal extremity of the hexapeptide of formula (I) are comprised between −1 and +1 per amino acid residue, preferably between −0.75 and +0.75 per amino acid residue.

Therefore, the subject matter of the present invention particularly concerns a compound or a pharmaceutical acceptable salt thereof as defined above, characterized in that the ionic partial charge on either the C-terminal and/or the N-terminal extremity of the hexapeptide of formula (I) are comprised between −1 and +1 per amino acid residue, preferably between −0.75 and +0.75 per amino acid residue, more preferably between −0.5 and +0.5 per amino acid residue, yet more preferably between −0.25 and +0.25 per amino acid residue. Indeed, surprisingly, getting rid of the extremity (N and/or C terminal) charges by known technics (such as acetylating heteroatoms e.g. amines or oxygens, or using aliphatic amino acids such as alanines, valines, leucines, isoleucines, norleucines . . . ) enables to increase the activity of the compounds without jeopardizing the solubility of said peptide sequence. One of the preferred embodiments of the present invention is thus to provide a peptide with little polar groups, i.e. no or little ionic charges, preferably on the extremities of the peptide. This of course can also depend of the pH of the environment. For example it would be possible to acetylate the N-terminal amine of the peptide structure, and bloc the C-terminal extremity with an amide (—CO—$NH_2$), thus reducing the extremity charges of the peptide structure.

Preferably, $X_2$ is a tyrosine residue, more preferably a paratyrosine.

Alternatively, $X_2$ is a phenylalanine residue, more preferably an unsubstituted phenyl alanine residue.

In a particular embodiment, the compound of formula (I) is a peptide comprising the sequence of formula (II):

$$\text{-A-B-}X_1\text{-}X_2\text{-}X_3\text{-}X_4\text{-}X_5\text{-}X_6\text{-} \quad (II)$$

wherein
A and B are amino acid residues, preferably natural or synthetic amino acid residues as defined above;
$X_1$, $X_2$, $X_3$, $X_4$, $X_5$ and $X_6$ are as defined presently;
or a pharmaceutical salt thereof.

Preferably in formula (II), A is a (D)-Lysine and B is an Arginine. Preferably in formula (II), A (such as (D)-Lysine) and B (such as (L)-Arginine) are linked to each other by a pseudopeptide bond, such as (—CO—NMe-). Preferably in formula (II) $X_1$-$X_2$-$X_3$-$X_4$-$X_5$-$X_6$ is FYVVXW, FYVVIW, FYVVKW or FYVVLW, wherein X is norleucine. Alternatively, in formula (II) $X_1$-$X_2$-$X_3$-$X_4$-$X_5$-$X_6$ is FFVVXW, FFVVIW, FFVVKW or FFVVLW, wherein X is norleucine In a particular embodiment, the compound of formula (I) is a peptide comprising the sequence of formula (III):

$$\text{-A-B-}X_1\text{-}X_2\text{-}X_3\text{-}X_4\text{-}X_5\text{-}X_6\text{-C-D-} \quad (III)$$

wherein
A, B, C and D are amino acid residues, preferably natural or synthetic amino acid residues as defined above;
$X_1$, $X_2$, $X_3$, $X_4$, $X_5$ and $X_6$ are as defined presently;
or a pharmaceutical salt thereof.

Preferably in formula (III), A is a (D)-Lysine and B is an Arginine. Preferably C is an (L)-Lysine and D is a (D)-Lysine. Preferably in formula (III), A (such as (D)-Lysine) and B (such as (L)-Arginine) are linked to each other by a pseudopeptide bond, such as (—CO—NMe-). Preferably in formula (III) $X_1$-$X_2$-$X_3$-$X_4$-$X_5$-$X_6$ is FYVVXW (SEQ ID 1), FYVVIW(SEQ ID 2), FYVVKW (SEQ ID 3) or FYVVLW (SEQ ID 4), wherein X is norleucine. Alternatively, in formula (III) $X_1$-$X_2$-$X_3$-$X_4$-$X_5$-$X_6$ is FFVVXW, FFVVIW, FFVVKW or FFVVLW, wherein X is norleucine.

Advantageously, the compound of formula (I) is a peptide comprising the sequence $X_1$-$X_2$-$X_3$-$X_4$-$X_5$-$X_6$ (formula (I)) and to sustain the solubility of the peptide of formula (I), the nature and the size of the structure is comprised between a peptide of 6 and 20 amino acids, more preferably between 7 and 15 amino acids, yet more preferably 8 and 12 amino acids, most preferably 10 amino acids. More preferably, the compound of formula (I) is a decapeptide (10 amino acids) with a dipeptide linked to the N-terminal extremity of the sequence $X_1$-$X_2$-$X_3$-$X_4$-$X_5$-$X_6$ (formula (I)) via a peptide or pseudopeptide bond, and a dipeptide linked to the C-terminal extremity of the sequence $X_1$-$X_2$-$X_3$-$X_4$-$X_5$-$X_6$ via a peptide or pseudopeptide bond on the N-terminal giving a formula (IV):

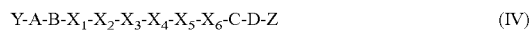

$$\text{Y-A-B-}X_1\text{-}X_2\text{-}X_3\text{-}X_4\text{-}X_5\text{-}X_6\text{-C-D-Z} \quad (IV)$$

wherein
A, B, C and D are amino acid residues, preferably natural or synthetic amino acid residues as defined above;
Y is a hydrogen, a $C_1$-$C_6$ alkyl group, a $C_5$-$C_8$ aryl group, a fragment $R_1$—CO— wherein $R_1$ is a hydrogen atom, a $C_1$-$C_6$ alkyl group, preferably a methyl, or a $C_5$-$C_8$ aryl group, preferably a phenyl;
Z is a —OH, $C_1$-$C_6$ alkyl group, a $C_5$-$C_8$ aryl group, a $NH_2$ group, a $C_1$-$C_6$ alkoxy group or a $C_5$-$C_8$ aryloxy group;
or a pharmaceutical salt thereof.

Preferably in formula (IV), all the amino residues on either sides of the peptide sequence $X_1$-$X_2$-$X_3$-$X_4$-$X_5$-$X_6$ are natural of (D) or (L) configuration and/or synthetic of (D) or (L) configuration amino acid residues as defined above. In a specific embodiment, the side chains and/or backbone of the compound of formula (I) are chemically protected according to the above definitions.

Preferably in formula (IV), A is a (D)-Lysine and B is an Arginine. Preferably C is an (L)-Lysine and D is a (D)-Lysine. Preferably in formula (IV), A (such as (D)-Lysine) and B (such as (L)-Arginine) are linked to each other by a pseudopeptide bond, such as (—CO—NMe-). Y is preferably in formula (IV) a hydrogen atom or an acetyl whilst Z is an $NH_2$. Preferably in formula (IV), $X_1$-$X_2$-$X_3$-$X_4$-$X_5$-$X_6$ is FYVVXW, FYVVIW, FYVVKW or FYVVLW, wherein X is norleucine. Alternatively in formula (IV), $X_1$-$X_2$-$X_3$-$X_4$-$X_5$-$X_6$ is FFVVXW, FFVVIW, FFVVKW or FFVVLW, wherein X is norleucine.

The present invention concerns a compound or the pharmaceutical acceptable salt thereof as presently disclosed, characterized in that $X_1$, $X_2$, $X_5$ and/or $X_6$ are non-ionic charged amino acid residues, such as $X_5$ is a norleucine, leucine or isoleucine residue, preferably a norleucine residue.

The present invention concerns a compound or the pharmaceutical acceptable salt thereof as presently disclosed, characterized in that the at least one pseudopeptide bond is an N-methyl peptide bond, preferably in a fragment linked to $X_1$ on the N-terminal side of the compound of formula (I) and/or in a fragment linked to $X_6$ on the C-terminal side of the compound of formula (I).

The present invention concerns a compound or the pharmaceutical acceptable salt thereof as presently disclosed, characterized in that a hydrogen atom, an amino acid residue or a peptide fragment is linked on the N-terminal amine of hexapeptide of formula (I).

The present invention concerns a compound or the pharmaceutical acceptable salt thereof as presently disclosed, characterized in that an —OH group, a —$NH_2$ group, an amino acid residue or a peptide fragment is linked to the C-terminal carbonyl of the hexapeptide of formula (I).

The present invention concerns a compound or the pharmaceutical acceptable salt thereof as presently disclosed, characterized in that the N-terminal amine of compound (I) or a pharmaceutical salt thereof is capped by a non-ionic charged group preferably chosen from the list consisting of a $C_1$-$C_6$ alkyl group, a $C_5$-$C_8$ aryl group, a fragment $R_1$—CO— wherein $R_1$ is:
a hydrogen atom,
a $C_1$-$C_6$ alkyl group, preferably a methyl or
a $C_5$-$C_8$ aryl group, preferably a phenyl.

The present invention concerns a compound or the pharmaceutical acceptable salt thereof as presently disclosed, characterized in that the C-terminal carboxylic acid has been replaced by a non-ionic charged group such as $COR_2$ wherein $R_2$ is a $C_1$-$C_6$ alkyl group, a $C_5$-$C_8$ aryl group, a $NH_2$ group, a $C_1$-$C_6$ alkoxy group or a $C_5$-$C_8$ aryloxy group.

The present invention concerns a compound or the pharmaceutical acceptable salt thereof as presently disclosed, characterized in that said compound or the pharmaceutical acceptable salt thereof comprises the sequence YVV, preferably in position $X_2$-$X_3$-$X_4$.

The present invention concerns a compound or the pharmaceutical acceptable salt thereof as presently disclosed, characterized in that $X_5$ is a lysine, norleucine, leucine or isoleucine.

The present invention concerns a compound or the pharmaceutical acceptable salt thereof as presently disclosed, characterized in that $X_5$ is a lysine, norleucine, leucine or isoleucine and $X_1$ is a phenylalanine.

The present invention concerns a compound or the pharmaceutical acceptable salt thereof as presently disclosed, characterized in that $X_5$ is a lysine, norleucine, leucine or isoleucine and $X_2$ is a tyrosine. The present invention concerns a compound or the pharmaceutical acceptable salt thereof as presently disclosed, characterized in that $X_5$ is a lysine, norleucine, leucine or isoleucine and $X_2$ is a phenylalanine.

The present invention concerns a compound or the pharmaceutical acceptable salt thereof as presently disclosed, characterized in that $X_5$ is a lysine, norleucine, leucine or isoleucine and $X_3$ is a valine.

The present invention concerns a compound or the pharmaceutical acceptable salt thereof as presently disclosed, characterized in that $X_5$ is a lysine, norleucine, leucine or isoleucine and $X_4$ is a valine.

The present invention concerns a compound or the pharmaceutical acceptable salt thereof as presently disclosed, characterized in that $X_5$ is a lysine, norleucine, leucine or isoleucine and $X_6$ is a tryptophan.

The present invention concerns a compound or the pharmaceutical acceptable salt thereof as presently disclosed, characterized in that $X_5$ is a lysine, norleucine, leucine or isoleucine, $X_1$ is a phenylalanine and $X_2$ is a tyrosine. The present invention concerns a compound or the pharmaceutical acceptable salt thereof as presently disclosed, characterized in that $X_5$ is a lysine, norleucine, leucine or isoleucine, $X_1$ is a phenylalanine and $X_2$ is a phenylalanine.

The present invention concerns a compound or the pharmaceutical acceptable salt thereof as presently disclosed, characterized in that $X_5$ is a lysine, norleucine, leucine or isoleucine, $X_1$ is a phenylalanine and $X_3$ is a valine.

The present invention concerns a compound or the pharmaceutical acceptable salt thereof as presently disclosed, characterized in that $X_5$ is a lysine, norleucine, leucine or isoleucine, $X_1$ is a phenylalanine and $X_4$ is a valine.

The present invention concerns a compound or the pharmaceutical acceptable salt thereof as presently disclosed, characterized in that $X_5$ is a lysine, norleucine, leucine or isoleucine, $X_1$ is a phenylalanine and $X_6$ is a tryptophan.

The present invention concerns a compound or the pharmaceutical acceptable salt thereof as presently disclosed, characterized in that $X_5$ is a lysine, norleucine, leucine or isoleucine, $X_1$ is a phenylalanine, $X_2$ is a tyrosine and $X_3$ is a valine. The present invention concerns a compound or the pharmaceutical acceptable salt thereof as presently disclosed, characterized in that $X_5$ is a lysine, norleucine, leucine or isoleucine, $X_1$ is a phenylalanine, $X_2$ is a phenylalanine and $X_3$ is a valine.

The present invention concerns a compound or the pharmaceutical acceptable salt thereof as presently disclosed, characterized in that $X_5$ is a lysine, norleucine, leucine or isoleucine, $X_1$ is a phenylalanine, $X_2$ is a tyrosine and $X_4$ is a valine. The present invention concerns a compound or the pharmaceutical acceptable salt thereof as presently disclosed, characterized in that $X_5$ is a lysine, norleucine, leucine or isoleucine, $X_1$ is a phenylalanine, $X_2$ is a phenylalanine and $X_4$ is a valine.

The present invention concerns a compound or the pharmaceutical acceptable salt thereof as presently disclosed, characterized in that $X_5$ is a lysine, norleucine, leucine or isoleucine, $X_1$ is a phenylalanine, $X_2$ is a tyrosine and $X_6$ is a tryptophan. The present invention concerns a compound or the pharmaceutical acceptable salt thereof as presently disclosed, characterized in that $X_5$ is a lysine, norleucine, leucine or isoleucine, $X_1$ is a phenylalanine, $X_2$ is a phenylalanine and $X_6$ is a tryptophan.

The present invention concerns a compound or the pharmaceutical acceptable salt thereof as presently disclosed, characterized in that $X_5$ is a lysine, norleucine, leucine or isoleucine, $X_1$ is a phenylalanine, $X_2$ is a tyrosine, $X_3$ is a valine and $X_4$ is a valine. The present invention concerns a compound or the pharmaceutical acceptable salt thereof as presently disclosed, characterized in that $X_5$ is a lysine, norleucine, leucine or isoleucine, $X_1$ is a phenylalanine, $X_2$ is a phenylalanine, $X_3$ is a valine and $X_4$ is a valine.

The present invention concerns a compound or the pharmaceutical acceptable salt thereof as presently disclosed, characterized in that $X_5$ is a lysine, norleucine, leucine or isoleucine, $X_1$ is a phenylalanine, $X_2$ is a tyrosine, $X_3$ is a valine and $X_6$ is a tryptophan. The present invention concerns a compound or the pharmaceutical acceptable salt thereof as presently disclosed, characterized in that $X_5$ is a lysine, norleucine, leucine or isoleucine, $X_1$ is a phenylalanine, $X_2$ is a phenylalanine, $X_3$ is a valine and $X_6$ is a tryptophan.

The present invention concerns a compound or the pharmaceutical acceptable salt thereof as presently disclosed, characterized in that $X_5$ is a lysine, norleucine, leucine or isoleucine, $X_1$ is a phenylalanine, $X_2$ is a tyrosine, $X_3$ is a valine $X_4$ is a valine and $X_6$ is a tryptophan. The present invention concerns a compound or the pharmaceutical acceptable salt thereof as presently disclosed, characterized in that $X_5$ is a lysine, norleucine, leucine or isoleucine, $X_1$ is a phenylalanine, $X_2$ is a phenylalanine, $X_3$ is a valine $X_4$ is a valine and $X_6$ is a tryptophan.

The present invention concerns a compound or the pharmaceutical acceptable salt thereof as presently disclosed, characterized in that said compound or the pharmaceutical acceptable salt thereof comprises the sequence YVV-norleucine (SEQ ID 5), preferably in position $X_2$-$X_3$-$X_4$-$X_5$.

The present invention concerns a compound or the pharmaceutical acceptable salt thereof as presently disclosed, characterized in that $X_1$, $X_2$, and/or $X_6$ is a para-fluoro-phenylalanine, para-amino-phenylalanine or para-nitro-phenylalanine.

The present invention concerns a compound or the pharmaceutical acceptable salt thereof as presently disclosed, characterized in that $X_1$ is a substitutes or unsubstituted phenylalanine, $X_2$ is a substituted or unsubstituted paratyrosine, and $X_6$ is a substituted or unsubstituted tryptophane. The present invention concerns a compound or the pharmaceutical acceptable salt thereof as presently disclosed, characterized in that $X_1$ is a substitutes or unsubstituted phenylalanine, $X_2$ is a substituted or unsubstituted phenylalanine, and $X_6$ is a substituted or unsubstituted tryptophane. The present invention concerns a compound or the pharmaceutical acceptable salt thereof as presently disclosed, characterized in that $X_1$ is a substitutes or unsubstituted phenylalanine, $X_2$ is a unsubstituted phenylalanine, and $X_6$ is a substituted or unsubstituted tryptophane.

The present invention concerns a compound or the pharmaceutical acceptable salt thereof as presently disclosed, characterized in that the hexapeptide of formula (I) is comprised between two amino acid residues of the (D) configuration, such as two (D)-lysines.

The present invention concerns a compound or the pharmaceutical acceptable salt thereof as presently disclosed, characterized in that it is chosen in the group consisting of:

```
                                          (SEQ ID 6)
H-KRFYGGMWKK-OH (SEQ ID 7)
Ac-RFYVVMWK-NH2

(SEQ ID 8)
Ac-KRFYVVMWKK-NH2

(SEQ ID 9)
H-(D)KRFYVVMWA(D)K-OH (SEQ ID 10)
H-(D)KAFYVVMWK(D)K-OH (SEQ ID 12)
H-(D)KRFYVV(Nle)WK(D)K-OH (SEQ ID 1)
H-FYVVXW-OH (SEQ ID 13)
H-FYVVXW-NH2

(SEQ ID 14)
Ac-FYVVXW-OH (SEQ ID 15)
Ac-FYVVXW-NH2

(SEQ ID 16)
H-(D)KFYVVXW(D)K-OH (SEQ ID 3)
H-FYVVKW-OH (SEQ ID 17)
H-FYVVKW-NH2

(SEQ ID 18)
H-(D)K ψ(CONMe)R F Y V V M W K (D)K-OH (SEQ ID 19)
H-(D)K R F Y V V M W ψ(CONMe)K (D)K-OH (SEQ ID 20)
H-(D)K ψ(CONMe)R F Y V V M W ψ(CONMe)K (D)K-OH (SEQ ID 21)
H-(D)K ψ(CONMe)R F Y V V X W K (D)K-OH (SEQ ID 22)
H-(D)K ψ(CONMe)R F Y V V L W K (D)K-OH (SEQ ID 23)
H-(D)K ψ(CONMe)R F Y VV I W K (D)K-OH (PKT16-FF)
H-(D)K ψ(CONMe)R F F V V X W K (D)K-OH
```

In the above peptides:
the "H" on the left hand side of the structures represents a hydrogen atom,
the term "Ac" means that the N-terminal amine is acetylated,
the "OH" on the right hand side of the structures represents the OH of the C-terminal COOH,
the "X" represents norleucine residue,
the "$NH_2$" on the right hand side of the structures means that the OH of the C-terminal COOH has been replaced by $NH_2$,
the (D) means that the following amino acid residue is of the (D) configuration, the terms "hR" and "hK" represent homo-arginine and homolysine respectfully,
"ψ(CONMe)" represent the pseudopeptide bond linking the two amino acid residues en either side of this term, and
Nle represents a norleucine residue.

In specific embodiments, it is contemplated that compounds of formula (I) used in the therapeutic methods of the present invention may be modified in order to improve their therapeutic efficacy. Such modification of therapeutic compounds may be used to decrease toxicity, increase circulatory time, or modify bio distribution. For example, the toxicity of potentially important therapeutic compounds can be decreased significantly by combination with a variety of drug carrier vehicles that modify bio distribution.

A strategy for improving drug viability is the utilization of water-soluble polymers. Various water-soluble polymers have been shown to modify bio distribution, improve the mode of cellular uptake, change the permeability through physiological barriers; and modify the rate of clearance from the body. To achieve either a targeting or sustained-release effect, water-soluble polymers have been synthesized that contain drug moieties as terminal groups, as part of the backbone, or as pendent groups on the polymer chain.

Polyethylene glycol (PEG) has been widely used as a drug carrier, given its high degree of biocompatibility and ease of modification. Attachment to various drugs, proteins, and liposomes has been shown to improve residence time and decrease toxicity. PEG can be coupled to active agents through the hydroxyl groups at the ends of the chain and via other chemical methods; however, PEG itself is limited to at most two active agents per molecule. In a different approach, copolymers of PEG and amino acids were explored as novel biomaterials which would retain the biocompatibility properties of PEG, but which would have the added advantage of numerous attachment points per molecule (providing greater drug loading), and which could be synthetically designed to suit a variety of applications.

Those of skill in the art are aware of PEGylation techniques for the effective modification of drugs. For example, drug delivery polymers that consist of alternating polymers of PEG and tri-functional monomers such as lysine have been used by VectraMed (Plainsboro, N.J.). The PEG chains (typically 2000 daltons or less) are linked to the a- and ε-amino groups of lysine through stable urethane linkages. Such copolymers retain the desirable properties of PEG, while providing reactive pendent groups (the carboxylic acid groups of lysine) at strictly controlled and predetermined intervals along the polymer chain. The reactive pendent groups can be used for derivatization, cross-linking, or conjugation with other molecules. These polymers are useful in producing stable, long-circulating pro-drugs by varying the molecular weight of the polymer, the molecular weight of the PEG segments, and the cleavable linkage between the drug and the polymer. The molecular weight of the PEG segments affects the spacing of the drug/linking group complex and the amount of drug per molecular weight of conjugate (smaller PEG segments provides greater drug loading). In general, increasing the overall molecular weight of the block co-polymer conjugate will increase the circulatory half-life of the conjugate. Nevertheless, the conjugate must either be readily degradable or have a molecular weight below the threshold-limiting glomular filtration (e.g., less than 45 kDa).

In addition, to the polymer backbone being important in maintaining circulatory half-life, and bio distribution, linkers may be used to maintain the therapeutic agent in a pro-drug form until released from the backbone polymer by a specific trigger, typically enzyme activity in the targeted tissue. For example, this type of tissue activated drug delivery is particularly useful where delivery to a specific site of bio distribution is required and the therapeutic agent is released at or near the site of pathology. Linking group libraries for use in activated drug delivery are known to those of skill in the art and may be based on enzyme kinetics, prevalence of active enzyme, and cleavage specificity of the selected disease-specific enzymes (see e.g., technologies of established by VectraMed, Plainsboro, N.J.). Such linkers may be used in modifying the soluble peptides-derived described herein for therapeutic delivery.

According to the invention, soluble peptides may be produced by conventional automated peptide synthesis methods or by recombinant expression. General principles for designing and making proteins are well known to those of skill in the art.

Soluble peptides of the invention may be synthesized in solution or on a solid support in accordance with conventional techniques. Various automatic synthesizers are commercially available and can be used in accordance with known protocols as described in Stewart and Young; Tarn et al, 1983; Merrifield, 1986 and Barany and Merrifield, Gross and Meienhofer, 1979. Soluble peptides of the invention may also be synthesized by solid-phase technology employing an exemplary peptide synthesizer such as a Model 433A from Applied Biosystems Inc. The purity of any given protein; generated through automated peptide synthesis or through recombinant methods may be determined using reverse phase HPLC analysis. Chemical authenticity of each peptide may be established by any method well known to those of skill in the art.

As an alternative to automated peptide synthesis for peptides containing only natural amino acids, recombinant DNA technology may be employed wherein a nucleotide sequence which encodes a protein of choice is inserted into an expression vector, transformed or transfected into an appropriate host cell and cultivated under conditions suitable for expression as described herein below. Recombinant methods are especially preferred for producing longer polypeptides.

A variety of expression vector/host systems may be utilized to contain and express the peptide or protein coding sequence. These include but are not limited to microorganisms such as bacteria transformed with recombinant bacteriophage, plasmid or cosmid DNA expression vectors; yeast transformed with yeast expression vectors (Giga-Hama et al, 1999); insect cell systems infected with virus expression vectors (e.g., baculovirus, see Ghosh et al., 2002); plant cell systems transfected with virus expression vectors (e.g., cauliflower mosaic virus, CaMV; tobacco mosaic virus, TMV) or transformed with bacterial expression vectors (e.g., Ti or pBR322 plasmid; see e.g., Babe et al, 2000); or animal cell systems. Those of skill in the art are aware of various techniques for optimizing mammalian expression of proteins, see e.g., Kaufman, 2000; Colosimo et al, 2000. Mammalian cells that are useful in recombinant protein productions include but are not limited to VERO cells, HeLa cells, Chinese hamster ovary (CHO) cell lines, COS cells (such as COS-7), W138, BHK, HepG2, 3T3, RIN, MDCK, A549, PC12, K562 and 293 cells. Exemplary protocols for the recombinant expression of the peptide substrates or fusion polypeptides in bacteria, yeast and other invertebrates are known to those of skill in the art and a briefly described herein below. U.S. Pat. Nos. 6,569,645; 6,043,344; 6,074,849; and 6,579,520 provide specific examples for the recombinant production of soluble peptides and these patents are expressly incorporated herein by reference for those teachings. Mammalian host systems for the expression of recombinant proteins also are well known to those of skill in the art. Host cell strains may be chosen for a particular ability to process the expressed protein or produce certain post-translation modifications that will be useful in providing protein activity. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, and the like have specific cellular machinery and characteristic mechanisms for such post-translational activities and may be chosen to ensure the correct modification and processing of the introduced, foreign protein.

In the recombinant production of the soluble peptides-derived of the invention, it would be necessary to employ vectors comprising polynucleotide molecules for encoding the soluble peptides-derived. Methods of preparing such vectors as well as producing host cells transformed with such vectors are well known to those skilled in the art. The polynucleotide molecules used in such an endeavor may be joined to a vector, which generally includes a selectable marker and an origin of replication, for propagation in a host. These elements of the expression constructs are well known to those of skill in the art. Generally, the expression vectors include DNA encoding the given protein being operably linked to suitable transcriptional or translational regulatory sequences, such as those derived from a mammalian, microbial, viral, or insect genes. Examples of regulatory sequences include transcriptional promoters, operators, or enhancers, mRNA ribosomal binding sites, and appropriate sequences which control transcription and translation.

The terms "expression vector," "expression construct" or "expression cassette" are used interchangeably throughout this specification and are meant to include any type of genetic construct containing a nucleic acid coding for a gene product in which part or all of the nucleic acid encoding sequence is capable of being transcribed.

The choice of a suitable expression vector for expression of the peptides or polypeptides of the invention will of course depend upon the specific host cell to be used, and is within the skill of the ordinary artisan. Methods for the construction of mammalian expression vectors are disclosed, for example, in Okayama and Berg, 1983; Cosman et al, 1986; Cosman et al, 1984; EP-A-0367566; and WO 91/18982. Other considerations for producing expression vectors are detailed in e.g., Makrides et al, 1999; Kost et al, 1999. Wurm et al, 1999 is incorporated herein as teaching factors for consideration in the large-scale transient expression in mammalian cells for recombinant protein production.

Expression requires that appropriate signals be provided in the vectors, such as enhancers/promoters from both viral and mammalian sources that may be used to drive expression of the nucleic acids of interest in host cells. Usually, the nucleic acid being expressed is under transcriptional control of a promoter. A "promoter" refers to a DNA sequence recognized by the synthetic machinery of the cell, or introduced synthetic machinery, required to initiate the specific transcription of a gene. Nucleotide sequences are operably linked when the regulatory sequence functionally relates to the DNA encoding the peptide of interest. Thus, a promoter nucleotide sequence is operably linked to a given DNA sequence if the promoter nucleotide sequence directs the transcription of the sequence.

Similarly, the phrase "under transcriptional control" means that the promoter is in the correct location and orientation in relation to the nucleic acid to control RNA polymerase initiation and expression of the gene. Any promoter that will drive the expression of the nucleic acid may be used. The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter. Common promoters include, e.g., the human cytomegalovirus (CMV) immediate early gene promoter, the SV40 early promoter, the Rous sarcoma virus long terminal repeat, [beta]-actin, rat insulin promoter, the phosphoglycerol kinase promoter and glyceraldehyde-3-phosphate dehydrogenase promoter, all of which are promoters well known and readily available to those of skill in the art, can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient to produce a recoverable yield of protein of interest. By employing a promoter with well-known properties, the level and pattern of expression of the protein of interest following transfection or transformation can be optimized. Inducible promoters also may be used.

Another regulatory element that is used in protein expression is an enhancer. These are genetic elements that increase transcription from a promoter located at a distant position on the same molecule of DNA. Where an expression construct employs a cDNA insert, one will typically desire to include a polyadenylation signal sequence to effect proper polyadenylation of the gene transcript. Any polyadenylation signal sequence recognized by cells of the selected transgenic animal species is suitable for the practice of the invention, such as human or bovine growth hormone and SV40 polyadenylation signals.

Acids nucleic, Vectors, recombinant host cells and uses thereof Another object of the invention relates to a nucleic acid encoding an amino acids sequence comprising the sequence of formula (I) or a function-conservative variant thereof as described here above for use in the prevention or treatment of cancer.

In one embodiment, said nucleic acid encoding an amino acids sequence consisting of the sequence of formula (I).

Nucleic acids of the invention may be produced by any technique known per se in the art, such as, without limitation, any chemical, biological, genetic or enzymatic technique, either alone or in combination(s).

Another object of the invention is an expression vector comprising a nucleic acid sequence encoding an amino sequence comprising the sequence of formula (I) or a function-conservative variant thereof as described here above for use in the prevention or treatment of cancer.

According to the invention, expression vectors suitable for use in the invention may comprise at least one expression control element operationally linked to the nucleic acid sequence. The expression control elements are inserted in the vector to control and regulate the expression of the nucleic acid sequence. Examples of expression control elements include, but are not limited to, lac system, operator and promoter regions of phage lambda, yeast promoters and promoters derived from polyoma, adenovirus, retrovirus, lentivirus or SV40. Additional preferred or required operational elements include, but are not limited to, leader sequence, termination codons, polyadenylation signals and any other sequences necessary or preferred for the appropriate transcription and subsequent translation of the nucleic acid sequence in the host system. It will be understood by one skilled in the art that the correct combination of required or preferred expression control elements will depend on the host system chosen. It will further be understood that the expression vector should contain additional elements necessary for the transfer and subsequent replication of the expression vector containing the nucleic acid sequence in the host system. Examples of such elements include, but are not limited to, origins of replication and selectable markers. It will further be understood by one skilled in the art that such vectors are easily constructed using conventional methods or commercially available. Another object of the invention is a host cell comprising an expression vector as described here above for use in the prevention or treatment of cancer.

According to the invention, examples of host cells that may be used are eukaryote cells, such as animal, plant, insect and yeast cells and prokaryotes cells, such as *E. coli*. The means by which the vector carrying the gene may be introduced into the cells include, but are not limited to, microinjection, electroporation, transduction, or transfection using DEAE-dextran, lipofection, calcium phosphate or other procedures known to one skilled in the art.

In another embodiment, eukaryotic expression vectors that function in eukaryotic cells are used. Examples of such vectors include, but are not limited to, viral vectors such as retrovirus, adenovirus, adeno-associated virus, herpes virus, vaccinia virus, poxvirus, poliovirus; lentivirus, bacterial expression vectors, plasmids, such as pcDNA3 or the baculovirus transfer vectors. Preferred eukaryotic cell lines include, but are not limited to, COS cells, CHO cells, HeLa cells, NIH/3T3 cells, 293 cells (ATCC # CRL1573), T2 cells, dendritic cells, or monocytes.

Therapeutic Methods

The subject matter of the present invention concerns as compound or a pharmaceutical acceptable salt according as presently defined for its use as a CD47 inhibitor, in particular in the treatment of cancer selected form the group consisting of adrenal cortical cancer, anal cancer, bile duct cancer, bladder cancer, bone cancer, brain and central nervous system cancer, breast cancer, Castleman disease, cervical cancer, colorectal cancer, endometrial cancer, esophagus cancer, gallbladder cancer, gastrointestinal carcinoid tumors, Hodgkin's disease, non-Hodgkin's lymphoma, Kaposi's sarcoma, kidney cancer, laryngeal and hypopharyngeal cancer, liver cancer, lung cancer, mesothelioma, plasmacytoma, nasal cavity and paranasal sinus cancer, nasopharyngeal cancer, neuroblastoma, oral cavity and oropharyngeal cancer, ovarian cancer, pancreatic cancer, penile cancer, pituitary cancer, prostate cancer, retinoblastoma, rhabdomyosarcoma, salivary gland cancer, skin cancer, stomach cancer, testicular cancer, thymus cancer, thyroid cancer, vaginal cancer, vulvar cancer, and uterine cancer, or in the prevention and the treatment of leukemia and particularly in acute lymphoblastic leukemia, B-chronic lymphocytic leukemia, hairy-cell leukemia, adult T-cell leukemia, prolymophocytic leukaemia of T-cell type or myeloid leukaemia.

In one embodiment, the leukemia is a B-chronic lymphocytic leukemia (CLL).

In a particular embodiment, soluble peptides, nucleic acids, expression vector or host cells of the invention may be useful in the treatment of a refractory CLL. In another particular embodiment, soluble peptides, nucleic acids, expression vector or host cells of the invention may be useful in the treatment of a refractory CLL with poor prognosis, including unmutated IGHV, complex karyotype and dysfunctional or mutated TP53, ATM, NOTH1, MYD88, XPO1, KLHL6, SF3B1, POTI and B IRC 3 B-cells.

As used herein, the term "refractory CLL" denotes a CLL refractory to common treatments used against leukemia (described in pages 2 and 3).

In a particular embodiment, soluble peptides, nucleic acids, expression vector or host cells of the invention may be useful in the treatment of refractory CLL that present intrinsic mutations that could allow to drug resistance (e.g, mutation/deletions in TP53, ATM, NOTH1, MYD88, XPO1, KLHL6, SF3B1, POTI and BIRC3 genes or refractory to the treatments described in pages 2 and 3).

Indeed, it was shown that B CLL cells that have the C481S mutation BTK gene (resistance to treatment with Ibrutinib) are sensitive to the treatment with PKT16 according to the present invention.

In a particular embodiment, soluble peptides, nucleic acids, expression vector or host cells of the invention may be useful in the treatment of refractory CLL where common treatment like anti-CD20, fludarabine or cladribine are not working.

Another object of the invention relates to a method for treating cancer comprising administering to a subject in need thereof a therapeutically effective amount of soluble peptides as described above or a nucleic acid according to the invention or an expression vector according to the invention or a host cell according to the invention.

In one aspect, the invention relates to a method for treating cancer comprising administering to a subject in need thereof a therapeutically effective amount of peptide of the sequence of formula (I) or a function-conservative variant thereof as above described.

In another embodiment, the invention relates to a method for treating cancer comprising administering to a subject in need thereof a therapeutically effective amount of a soluble peptide according to the invention.

Pharmaceutical Composition

Another object of the invention is a pharmaceutical composition for use in the treatment of cancer comprising:
a) at least one compound of formula (1) according to the invention;
b) at least one acids nucleic according to the invention; or
c) at least one expression vector according to the invention or;
d) at least one host cell according to the invention;
e) and a pharmaceutically acceptable carrier.

In one embodiment, said pharmaceutical composition comprises at least one compound of formula (I) with a hexapeptide having the sequence of formula (I), embedded within.

In another embodiment, said pharmaceutical composition comprises a function-conservative variant thereof of the compound of formula (I) with a hexapeptide having the sequence of formula (I), embedded within.

In still another embodiment, said pharmaceutical composition comprises the peptide PKT16, or PKT16-FF.

Any therapeutic agent of the invention as above described may be combined with pharmaceutically acceptable excipients, and optionally sustained-release matrices, such as biodegradable polymers, to form therapeutic compositions.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, intranasal, intraocular, intravenous, intramuscular or subcutaneous administration and the like.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

To prepare pharmaceutical compositions, an effective amount of a polypeptide or a nucleic acid according to the invention may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, mixtures thereof and in oils. Under ordinary conditions of storage and use, these preparations contain a preservative to prevent the growth of microorganisms.

The peptides thereof or the nucleic acid according to the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution may be suitably buffered and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

In addition to the compounds formulated for parenteral administration, such as intravenous or intramuscular injection, other pharmaceutically acceptable forms include, e.g. tablets or other solids for oral administration; time release capsules; and any other form currently used.

In one embodiment, the pharmaceutical composition may comprise cells stably expressing a peptide or variant thereof according to the invention. For example, the pharmaceutical composition may comprise HEK293T cells stably expressing the peptide of the invention polypeptide, or HCT116 cells stably expressing the peptide of the invention. The cells may be encapsulated in alginate gel beads, as described in Desille et al, 2001, 2002 and Mahler et al, 2003. This vectorization approach enables a localized delivery of the polypeptide of the invention.

Compositions of the present invention may comprise a further therapeutic active agent.

The present invention also relates to a kit comprising a compound of formula (I) with a hexapeptide having the sequence of formula (I), embedded within according to the invention and a further therapeutic active agent.

In one embodiment said therapeutic active agent is an anticancer agent. For example, said anticancer agents include but are not limited to fludarabine, gemcitabine, capecitabine, methotrexate, taxol, taxotere, mercaptopurine, thioguanine, hydroxyurea, cytarabine, cyclophosphamide, ifosfamide, nitrosoureas, platinum complexes such as cisplatin, carboplatin and oxaliplatin, mitomycin, dacarbazine, procarbazine, etoposide, teniposide, campathecins, bleomycin, doxorubicin, idarubicin, daunorubicin, dactinomycin, plicamycin, mitoxantrone, L-asparaginase, doxorubicin, epimbicm, 5-fluorouracil, taxanes such as docetaxel and paclitaxel, leucovorin, levamisole, irinotecan, estramustine, etoposide, nitrogen mustards, BCNU, nitrosoureas such as carmustme and lomustine, *vinca* alkaloids such as vinblastine, vincristine and vinorelbine, imatimb mesylate, hexamethyhnelamine, topotecan, kinase inhibitors, phosphatase inhibitors, ATPase inhibitors, tyrphostins, protease inhibitors, inhibitors herbimycm A, genistein, erbstatin, and lavendustin A. In one embodiment, additional anticancer agents may be selected from, but are not limited to, one or a combination of the following class of agents: alkylating agents, plant alkaloids, DNA topoisomerase inhibitors, antifolates, pyrimidine analogs, purine analogs, DNA antimetabolites, taxanes, podophyllotoxin, hormonal therapies, retinoids, photo sensitizers or photodynamic therapies, angiogenesis inhibitors, antimitotic agents, isoprenylation inhibitors, cell cycle inhibitors, actinomycins, bleomycins, anthracyclines, MDR inhibitors and $Ca^{2+}$ ATPase inhibitors.

Additional anticancer agents may be selected from, but are not limited to, cytokines, chemokines, growth factors, growth inhibitory factors, hormones, soluble receptors, decoy receptors, monoclonal or polyclonal antibodies, mono-specific, bi-specific or multi-specific antibodies, monobodies, polybodies.

Additional anticancer agent may be selected from, but are not limited to, growth or hematopoietic factors such as erythropoietin and thrombopoietin, and growth factor mimetics thereof.

In the present methods for treating cancer the further therapeutic active agent can be an antiemetic agent. Suitable antiemetic agents include, but are not limited to, metoclopromide, domperidone, prochlorperazine, promethazine, chlorpromazine, trimethobenzamide, ondansetron, granisetron, hydroxyzine, acethylleucine monoemanolamine, alizapride, azasetron, benzquinamide, bietanautine, bromopride, buclizine, clebopride, cyclizine, dunenhydrinate, diphenidol, dolasetron, meclizme, methallatal, metopimazine, nabilone, oxypemdyl, pipamazine, scopolamine, sulpiride, tetrahydrocannabinols, thiefhylperazine, thioproperazine and tropisetron. In a partucular embodiment, the antiemetic agent is granisetron or ondansetron.

In another embodiment, the further therapeutic active agent can be an hematopoietic colony stimulating factor. Suitable hematopoietic colony stimulating factors include, but are not limited to, filgrastim, sargramostim, molgramostim and epoietin alpha.

In still another embodiment, the other therapeutic active agent can be an opioid or non-opioid analgesic agent. Suitable opioid analgesic agents include, but are not limited to, morphine, heroin, hydromorphone, hydrocodone, oxymorphone, oxycodone, metopon, apomorphine, nomioiphine, etoipbine, buprenorphine, mepeddine, lopermide, anileddine, ethoheptazine, piminidine, betaprodine, diphenoxylate, fentanil, sufentanil, alfentanil, remifentanil, levorphanol, dextromethorphan, phenazodne, pemazocine, cyclazocine, methadone, isomethadone and propoxyphene. Suitable non-opioid analgesic agents include, but are not limited to, aspirin, celecoxib, rofecoxib, diclofinac, diflusinal, etodolac, fenoprofen, flurbiprofen, ibuprofen, ketoprofen, indomethacin, ketorolac, meclofenamate, mefanamic acid, nabumetone, naproxen, piroxicam and sulindac.

In yet another embodiment, the further therapeutic active agent can be an anxiolytic agent. Suitable anxiolytic agents include, but are not limited to, buspirone, and benzodiazepines such as diazepam, lorazepam, oxazapam, chlorazepate, clonazepam, chlordiazepoxide and alprazolam.

The invention will be further illustrated by the following figures and examples.

However, these examples and figures should not be interpreted in any way as limiting the scope of the present invention.

FIG. 1: Peptide degradation assay.

Four peptides (1, 2, 3 and 4) were designed in order to improve the human serum stability, which was determined by following peptide degradation after incubation at 37° C. during two hours. 4NGG: inactive analogue of 4N1K where both valine of the VVM sequence have been mutated by two glycines (see Manna, P. P. et al.; J. Immunol. 2003, 170: 3544-3553).

FIGS. 2A and 2B: PKT16, a PKHB1-derivative peptide with improved PCD activity in CLL cells.

FIG. 2A: cell death, measured as Annexin-V and PI co-positivity, was assessed leukemic cells treated 6 h with different concentrations of PKT16 or PKHB1. The data in the plot are the mean±s.d. (n=5). FIG. 2B: cell death induced by PKT16 (100 µM, 6 h) was measured in B-cells from twenty healthy donors and forty CLL patients. The percentages refer to the mean of the Annexin-V/PI-positive staining FIG. 3: CD spectroscopy performed in PBS or in water The conformational propensity of each peptide was then examined by CD spectroscopy in FIG. 3. Peptides exhibit no helical propensity and a small β-sheet content can be observed only for the least soluble 4N1 and PKT1 peptides, suggesting that the b-structure arises from aggregated species.

Figure 4:
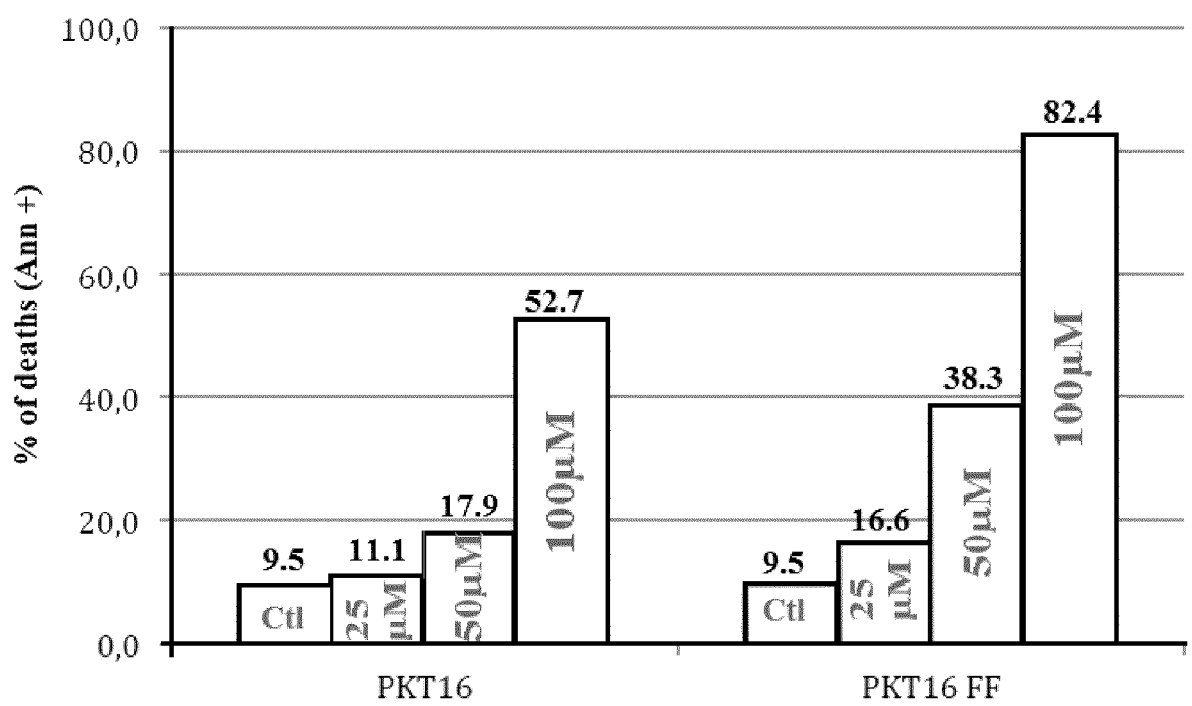

FIG. 4: compares deaths on OSU cells treated with PKT16 or PKT16-FF. For PKT16, it can be seen that the reported deaths are of 11.1, 17.9 and 52.7% for concentrations of 25 µM, 50 µM and 100 µM respectively. For PKT16-FF, it can be seen that the reported deaths are of 16.6, 38.3 and 82.4% for concentrations of 25 µM, 50 µM and 100 µM respectively. The control test provided 9.5% death of the cells.

EXAMPLES

Preamble: Synthesis and Characterization of the Peptides Chemistry.

All the peptides were synthesized manually from Fmoc-protected amino acids utilizing standard solid phase peptide synthesis (SPPS) methods. The appropriate protected amino acids were sequentially coupled using HBTU/HOBT as an activator. The peptides were cleaved from the resin with (94:1:2.5:2.5) TFA/TIS/$H_2O$/EDT. The crude products were purified using RP-HPLC. The final products were characterized by analytical RP-HPLC, LCMS and NMR. All tested compounds were trifluoroacetate salts and were at least 95% pure. Detailed NMR studies were performed for the relevant peptides.

Chemicals:

All commercial chemicals and solvents were reagent grade and were used without further purification unless otherwise specified. All reactions except those in aqueous media were carried out with the use of standard techniques for the exclusion of moisture. All reactions were performed under argon or nitrogen in oven-dried glassware using anhydrous solvents and standard syringe techniques. ß2-homolysine and homoarginine were synthesized as previously reported.i Peptide synthesis transformations and washes were performed at 20° C. All Fmoc carbamate protected amino acid derivatives, HATU, HOAt, HBTU, HOBt, Fmoc-Rink Amide (200-400 mesh, loading 0.62 mmol/g) and 2-CTC resin (100-200 mesh, loading 1.6 mmol/g) were purchased from Iris Biotech (Marktredwitz, Germany). Reagents such as DIEA, piperidine, DMF, IPA, Ac2O, MeOH, TFA and TIS were obtained from Sigma-Aldrich (Saint Louis, USA). Compounds molecular weights were calculated using ChemBioDraw® Ultra 12. All final products were of >95% purity unless otherwise indicated (determined by analytical reverse phase LC-MS). Analytical data are given in Table 6 (example 6) as an illustration for two potent peptides according to the present invention.

Analytics:

Two methods were conducted for LC-MS analysis.

Method A: analytical HPLC was conducted on a X-Select CSH C18 XP column (30×4.6 mm id, 2.5 µm) eluting with 0.1% formic acid in water (solvent A) and 0.1% formic acid in acetonitrile (solvent B), using the following elution gradient 0-3.2 min: 0% to 50% B, 3.2-4 min 100% B, at a flow rate of 1.8 mL/min at 40° C. The mass spectra (MS) were recorded on a Waters ZQ mass spectrometer using electrospray positive ionisation [ES+ to give (MH)+ molecular ions] or electrospray negative ionisation [ES− to give (MH)− molecular ions] modes. The cone voltage was 20 V.

Method B: analytical HPLC was conducted on a X-Select CSH C18 XP column (30×4.6 mm id, 2.5 µm) eluting with 0.1% formic acid in water (solvent A) and 0.1% formic acid in acetonitrile (solvent B), using the following elution gradient 0-3.2 min: 5% to 100% B, 3.2-4 min: 100% B, at a flow rate of 1.8 mL/min at 40° C. The mass spectra (MS) were recorded on a Waters ZQ mass spectrometer using electrospray positive ionisation [ES+ to give (MH)+ molecular ions] or electrospray negative ionisation [ES- to give (MH)− molecular ions] modes. The cone voltage was 20 V.

Purification:

Preparative scale purification of peptides was performed by reverse phase HPLC on a Waters system consisted of a quaternary gradient module (Water 2535) and a dual wavelength UV/Visible Absorbance detector (Waters 2489), piloted by Empower Pro 3 software using the following columns: preparative Macherey-Nagel column (Nucleodur HTec, C18, 250×16 mm id, 5 µm, 110 Å) and preparative Higgins Analytical column (Proto 200, C18, 150×20 mm id, 5 µm, 200 Å) at a flow rate of 14 mL/min and 20 mL/min respectively. Small-scale crudes (<30 mg) were purified using semi-preparative Ace column (Ace 5, C18, 250×10 mm id, 5 µm, 300 Å) at a flow rate of 5 mL/min. Purification gradients were chosen to get a ramp of approximately 1% solution B per minute in the interest area and UV detection was done at 220 nm and 280 nm. Peptide fractions from purification were analyzed by LC-MS (method A or B depending of retention time) or by analytical HPLC on a Dionex system consisted of an automated LC system (Ultimate 3000) equipped with an auto sampler, a pump block composed of two ternary gradient pumps and a dual wavelength detector, piloted by Chromeleon software. All LC-MS or HPLC analyses were performed on C18 columns. The pure fractions were gathered according to their purity and then freeze-dried using an Alpha 2/4 freeze dryer from Bioblock Scientific to get the expected peptide as a white powder. Final peptide purity (>95%) of the corresponding pooled fractions was checked by LC-MS using method A.

Manual Loading of the First Amino Acid:

Solid-phase peptide syntheses were performed in polypropylene Torviq syringes (10 or 20 mL) fitted with a polyethylene porous disc at the bottom and closed with an appropriate piston. Solvent and soluble reagents were removed through back and forth movements. The 2-CTC resin was previously swelled in strictly anhydrous DCM (distilled) for 2 h. Side-chain protected Fmoc-Aa-OH (0.30 mmol, 1 eq.) was coupled to 2-CTC resin (400 mg, loading 1.6 mmol/g) in the presence of DIEA (1.2 mmol, 4 eq.) in DCM (4 mL). The unreacted sites on the resin were capped by washing with a mixture of DCM/MeOH/DIEA (17:2:1) repeated 3 times. Thus loading was reduced to 0.80 mmol/g for optimal peptide growth. In the case of Rink Amide resin, swollen in DCM was done similarly in 2 h (500 mg, loading 0.62 mmol/g). However, first coupling was directly performed with protected Fmoc-Aa-OH (1.2 mmol, 4 eq.), HBTU (1.2 mmol, 4 eq.), HOBt (1.2 mmol, 4 eq.) and DIEA (2.4 mmol, 8 eq.) without loading decreasing.

Manual Solid Phase Peptide Synthesis:

In all syntheses the scale was 0.30 mmol. Fmoc group was split off by treatment with piperidine/DMF (1:4) (1×1 min, 1×10 min). Washing steps between deprotection and coupling were carried out with DMF (3×1 min), IPA (3×1 min) and DMF (3×1 min). Activation step was carried out with Fmoc-Aa-OH (1.2 mmol, 4 eq.), HBTU (1.2 mmol, 4 eq.) as coupling agent, HOBt (1.2 mmol, 4 eq.) as auxiliary nucleophile, and DIEA (2.4 mmol, 8 eq.) as base. The activated amino acid is then transferred to the resin where the coupling was performed for 1 to 18 h. Supported coupling reactions were monitored by classical Kaiser test (solution kit from Sigma-Aldrich). When elongation of the peptide chain was completed, a MeOH washing step was added after final N-terminal Fmoc removal for complete shrinkage of the resin under vacuum.

Site-Selective N-Methylation of Peptide Backbone:

Residue was N-methylated on solid-phase through Kessler's conditions: first, the free amino functionality was protected and activated with the o-nitrobenzenesulfonyl (o-NBS) group, then N-methylated using 1,8-diazabicyclo [5,4,0]undec-7-ene (DBU) and dimethylsulfate (DMS), and finally deprotected (removal of o-NBS) by treating the resin with βmercaptoethanol and DBU.

o-NBS Protection:

A solution of o-NBS-Cl (4 eq.) and collidine (10 eq.) in NMP was added to the resin-bound free amine peptides and shaken for 15 min at room temperature. The resin was washed with NMP (5×).

N-Methylation with DBU and DMS:

A solution of DBU (3 eq.) in NMP was added to the resin bound o-NBS-protected peptides and shaken for 3 min. A solution of dimethylsulfate (10 eq.) in NMP was then added to the reaction mixture and shaken for 2 min. The resin was filtered off, washed once with NMP and the N-methylation procedure repeated once more. The resin was washed with NMP (5×).

o-NBS Deprotection: The resin bound Nα-methyl-Nα-o-NBS-peptides was treated with a solution of β-mercaptoethanol (10 eq.) and DBU (5 eq.) in NMP for 5 min. The deprotection procedure was repeated once more and the resin was washed with NMP (5×). [Biron, E.; Chatterjee, J.; Kessler, H. *J. Peptide Sci.* 2006, 12, 213 and references cited therein]

Final Side-Chain Deprotection and Cleavage from the Resin:

The crude peptides were treated with the following cleavage cocktail: TFA/H2O/TIS (95/2.5/2.5, 10 mL). The syringes were shaken for 3 h and then precipitated 3 times using cooled Et2O (3×30 mL), recovered after centrifugations (3×5 min, 7800 rpm), diethyl ether was removed (3 times), and then the peptide pellets were dried (under nitrogen flow). The resulting crude peptide was dissolved in aqueous 0.1% (v/v) TFA. Purification was conducted on reversed-phase HPLC Prep C18 column, eluting with 0.1% TFA in water (solvent A) and 0.1% TFA in acetonitrile (solvent B) as described earlier.

Peptide Degradation Assays.

The peptides (10 mg/mL), diluted in a 1:4 human serum/ RPMI 1640 mixture, were incubated at 37° C. at different times, then mixed with ethanol and 5 mL of 1M NaOH and incubated at 4° C. for at least 15 min to precipitate serum proteins. The supernatant was collected, injected in an HPLC and the soluble peptide was eluted by a linear gradient 5 to 50% ACN [0.1% (v/v) TFA in acetonitrile] in aqueous 0.1% (v/v) TFA. The concentration of the peptide was calculated by integrating the absorbance at 220 nm as a function of the retention time.

Cd Spectroscopy.

CD spectra were recorded on a Jasco 815 spectropolarimeter (Jasco Inc., Easton, Md.) over the wavelength range 190-260 nm, at 0.2 nm intervals and 10 nm·min$^{-1}$ scan speed. Peptides were dissolved at 50 µM concentration in a 10 mM sodium phosphate buffer at pH 7.4, using 0.1 cm path length quartz cells (Hellma, Mullheim, Germany). CD spectra were deconvoluted with CDFriend program in order to estimate the peptide secondary structure content.

NMR Conformational Analysis.

NMR experiments were recorded on a 500 MHz Bruker Avance III spectrometer (Wissembourg, France) equipped with a TCI cryoprobe. NMR samples were prepared in 50 mM sodium succinate buffer, pH 5, using 2 mM peptide concentration. Sodium 2,2-dimethyl-2-silapentane-d$_6$-5-sulfonate (Sigma Aldrich) was added at 0.1 mM concentration for chemical shift calibration and measurement of the solubilized peptide concentration. NMR experiments were processed with TOPSPIN 2.1 software (Bruker) and spectra were analyzed with Sparky program. $^1$H, $^{13}$C and $^{15}$N resonances were assigned using 2D $^1$H-$^1$H TOCSY (DIPSI2 isotropic scheme of 70 ms duration), 2D $^1$H-$^1$H ROESY (300 ms mixing time), 2D $^1$H-$^{13}$C HSQC, 2D $^1$H-$^{15}$N HSQC, and 2D $^1$H-$^{13}$C HMBC spectra. The complete $^1$H, $^{13}$C and $^{15}$N NMR assignments of peptides 4N1K, PKT2, PKHB1 and 4NGG are provided in Tables S1-S4 (supporting information). For the three poorly soluble peptides 4N1, PKT1 and PKHB3, only partial $^1$H assignments could be obtained (Tables S5-S7). $^3J_{HN-H\alpha}$ coupling constants were measured on 1D $^1$H WATERGATE experiments. The chemical shift deviations of Hα protons and Cα carbons were calculated as the differences between observed chemical shifts and random coil values reported in water. The conformational analysis of thrombospondin-1 was carried out on the crystal structure of a C-terminal fragment of human thrombospondin-1 using Pymol (Schrödinger) and Procheck programs. Predictions of NMR chemical shifts on the X-ray structure were carried out using SHIFTX2 program.

Biological Assays.

Binding Affinity Measurements.

The binding affinities of peptides for a membrane preparation from MEC-1 cells were measured by biolayer interferometry on an Octet RED96 System (Pall FortéBio Corp., Menlo Park, Calif.).

Binding Affinity Measurements by Biolayer Interferometry.

The binding affinities of peptides for a membrane preparation from MEC-1 cells were measured by biolayer interferometry on an Octet RED96 System (Pall FortéBio Corp., Menlo Park, Calif.). This system monitors interference of light reflected from two sources (an internal reflection surface and the liquid/solid interface of a fiber optic sensor) to measure the rate of binding of molecules to the biosensor surface.

MEC-1 cell membrane preparation were biotinylated with the EZ-Link NHS-PEG4-Biotin kit from Thermo-Scientific. Biotinylated membranes were then loaded onto Super-Streptavidin (SSA) biosensors (Pall FortéBio Corp.) at empirically determined concentrations. All affinity measurements were carried out in assay buffer (PBS with 0.2% bovine serum albumine and 1% dimethyl sulfoxyde) at 30° C.

Example 1: First Generation of Peptide Compounds

Here, the ability of 4N1K to induce selective PCD in cancer cell lines while sparing normal cells was explored. Considering its potential as a therapeutic approach to treat cancer, even from refractory patients with TP53 deletion, its serum stability and designed analogues resistant to proteases was explored. In order to highlight the pharmacological properties of these peptides, a systematic SAR study by the development of a binding assay allowing to the assessment of the affinity of the 4N1K analogues to CD47 was initiated. Conformational studies by CD and NMR were realized and the data were compared to the X-ray structure of the 4N1 sequence in the context of the TSP-1 protein. An Ala-scan to identify the pharmacophores of 4N1K was implemented. Peptide degradation assay of these peptides is reported in FIG. 1.

The following peptides were thus synthesized using common solid phase synthesis methods (as described above):

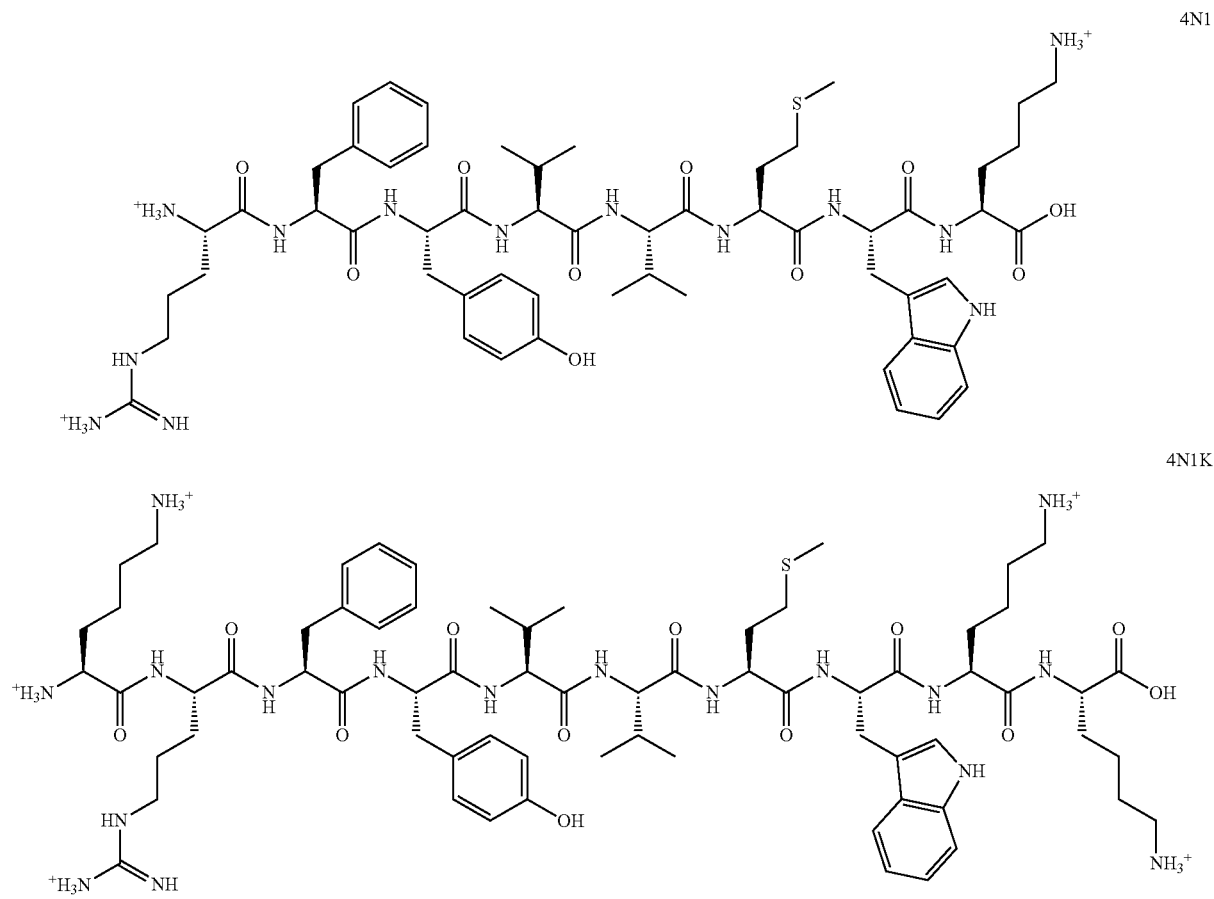

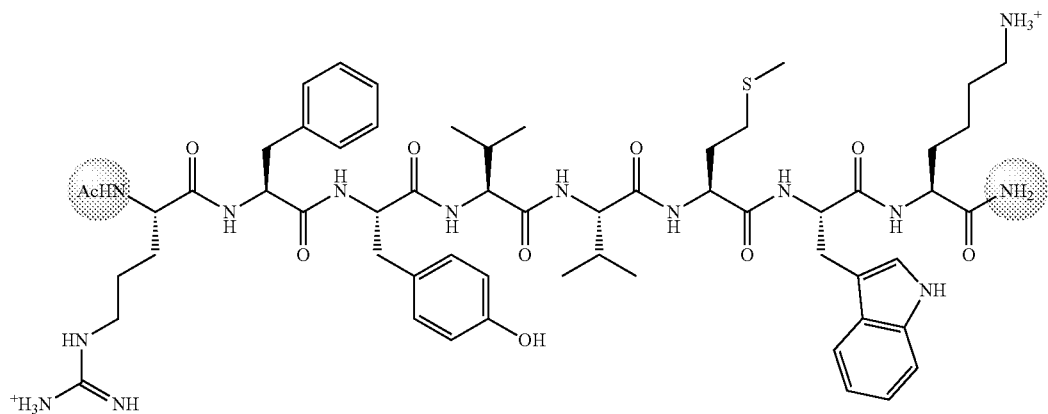
1
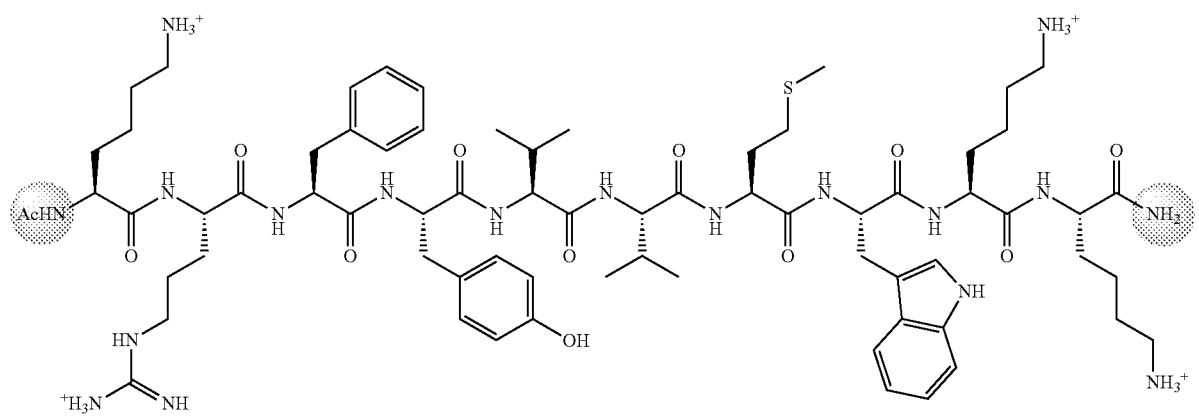
2
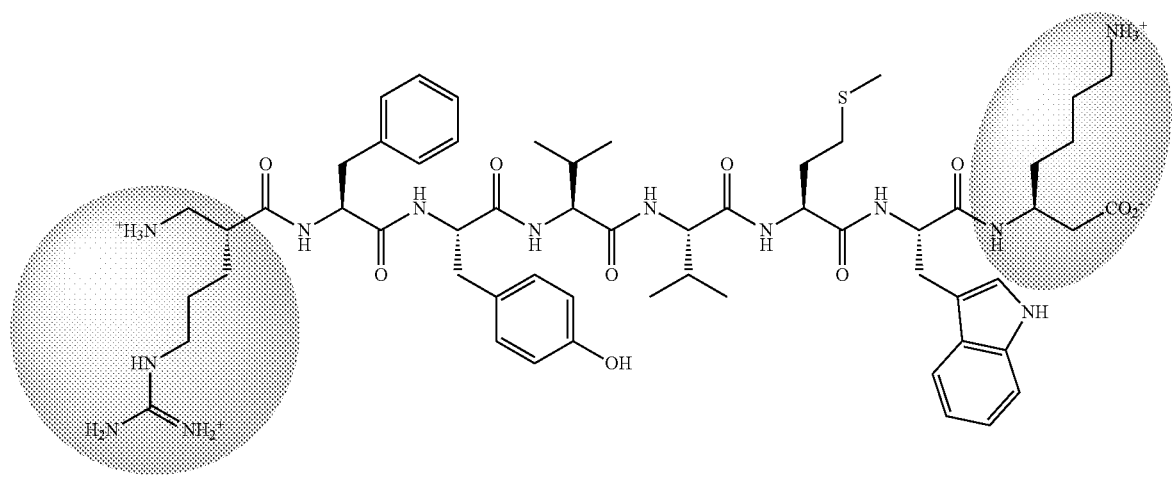
3

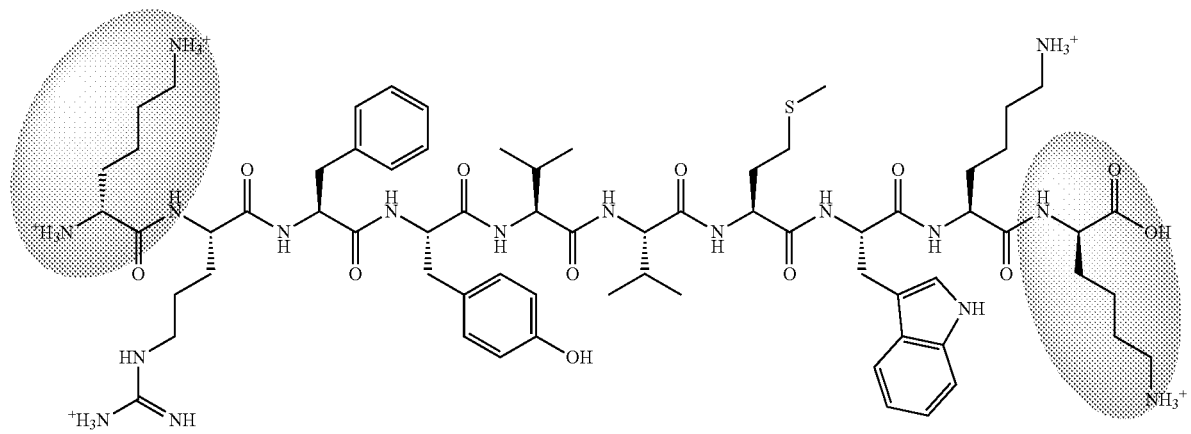

Then the peptides structures were tested via NMR and X-ray. The peptides were also tested for their activity on MEC-1 and their $K_D$s and Retention times on LCMS were determined.

TABLE 1

Comparison of experimental NMR $^3$JHN-Hα coupling constants with J-coil and values inferred from X-ray structure

| Residue | J-coil[a] | 4N1K | 4 | 2 | 4NGG | X-ray[b] |
|---|---|---|---|---|---|---|
| Arg2 | 6.92 | 7.0 | br s | 7.2 | br s | 9.1 |
| Phe3 | 7.35 | 7.9 | 7.4 | 7.9 | 8.0 | 4.6 |
| Tyr4 | 7.32 | 7.9 | 7.8 | 7.8 | 7.8 | 8.9 |
| Val5 | 7.55 | 8.1 | 8.1 | 8.0 | (Gly) | 9.2 |

TABLE 1-continued

Comparison of experimental NMR $^3$JHN-Hα coupling constants with J-coil and values inferred from X-ray structure

| Residue | J-coil[a] | 4N1K | 4 | 2 | 4NGG | X-ray[b] |
|---|---|---|---|---|---|---|
| Val6 | 7.55 | 7.8 | 7.9 | 7.6 | (Gly) | 9.8 |
| Met7 | 6.97 | 7.4 | 7.3 | 7.1 | 7.3 | 9.5 |
| Trp8 | 7.01 | 7.0 | n.d. | 6.8 | n.d. | 9.4 |
| Lys9 | 6.92 | 7.4 | 7.5 | 7.3 | n.d. | 9.6 |
| Lys10 | 6.92 | 7.3 | 7.9 | 6.6 | n.d. | |

[a]Average coupling constants from the coil library taken from reference "Avbelj, F. et al. Proc. Natl. Acad. Sci. USA 2006, 103, 1272-1277".
[b]Values calculated on 1UX6 crystal structure using the Karplus relationship from reference Vuister, C. W. et al. J. Am. Chem. Soc. 1993, 115, 7772-7777.

TABLE 2

Structure characterization, affinity and activity of the peptides designed to improve stability

| Peptides | Sequence | Kd[a] (µM) (OR) | Kd[a] (µM) (MST) | MEC-1 Cell Death (%)[b] 2 h |
|---|---|---|---|---|
| 4N1 | RFYVVMWK (SEQ ID 24) | NPD | 10 ± 0.8 | 13% |
| 1 | Ac-RFYVVMWK-NH$_2$ (SEQ ID 25) | 1.5 ± 0.59 | 0.771 ± 0.07 | 27% |
| 3 | (β$^2$hR)FYVVMW(β$^3$hK) (SEQ ID 11) | NPD | NPD | NPD |
| 4N1K | KRFYVVMWKK (SEQ ID 26) | 19 ± 1.6 | 2.28 +/- 0.22 | 23% |
| 4NGG | KRFYGGMWKK (SEQ ID 6) | NPD | NPD | 2% |
| 2 | Ac-KRFYVVMWKK-NH$_2$ (SEQ ID 8) | 40 ± 24 | 1.2 ± 0.16 | 30% |
| 4 (PKHB1) | kRFYVVMWKk (SEQ ID 27) | 43 ± 21 | 3.04 ± 0.25 | 63% |

[a,b]Reported Kd values and % of PCD are an average of, at least, three independent experiments, NPD: Non Pertinent Data.
[c]5% to 100% over 55 min of acetonitrile/water containing 0.1% TFA.

TABLE 3

Structure characterization, affinity and activity of the peptides designed for the pharmacophores identification

| peptides | Structure | SEQ ID No | $t_R$ (min)[e] | $Kd^a$ (µM) | MEC-1 Cell Death (%)[b] 2 h, [peptides] = 200 µM |
|---|---|---|---|---|---|
| 4 (PKHB1) | kRFYVVMWKk | 27 | 1.54 | 43 ± 21 | 63% |
| 4N1K | KRFYVVMWKK | 26 | 1.52 | 19 ± 1.6 | 23% |
| R2/A | k(A)FYVVMWKk | 28 | 1.76 | 6.2 ± 1.9 | 44% |
| F3/A | kR(A)YVVMWKk | 34 | 1.34 | NPD | 6% |
| Y4/A | kRF(A)VVMWKk | 35 | 1.47 | NPD | 0% |
| V5/A | kRFY(A)VMWKk | 36 | 1.47 | NPD | 12% |
| V6/A | kRFYV(A)MWKk | 37 | 1.49 | NPD | 30% |
| M7/A | kRFYVV(A)WKk | 38 | 1.48 | 42 ± 21 | 6% |
| W8/A | kRFYVVM(A)Kk | 39 | 1.28 | NPD | 35% |
| K9/A | kRFYVVMW(A)k | 40 | 1.83 | 27 ± 21 | 46% |
| M/Nle[d] | kRFYVV(Nle)WKk | 41 | 1.71 | 18 ± 0.6 | 47% |

[a,b]Reported Kd values and % cell death are an average of two or more measurements,
NPD: Non Pertinent Data.
[c]5% to 100% over 55 min of acetonitrile/water containing 0.1% TFA.
[d]Nle: Norleucine.
[e]Retention times are indicated for LCMS method A.

Method A: Two methods were conducted for LC-MS analysis. Method A: analytical HPLC was conducted on a X-Select CSH C18 XP column (30×4.6 mm id, 2.5 µm) eluting with 0.1% formic acid in water (solvent A) and 0.1% formic acid in acetonitrile (solvent B), using the following elution gradient 0-3.2 min: 0% to 50% B, 3.2-4 min 100% B, at a flow rate of 1.8 mL/min at 40° C. The mass spectra (MS) were recorded on a Waters ZQ mass spectrometer using electrospray positive ionisation [ES+ to give (MH)+ molecular ions] or electrospray negative ionisation [ES− to give (MH)− molecular ions] modes. The cone voltage was 20 V.

Example 2: Second Generation of Peptide Compounds

N-methyl amino acids were utilized in the design of PKT16 to disrupt the peptide-peptide interaction that promotes the aggregation. Indeed, the replacement of the amide proton by a methyl group seems to prevent the hydrogen bonding interactions that normally stabilizes the β-sheet through interactions between individual β-strands. Moreover, N-methyl amino acids seem to prevent the close approach of β-strands because of steric hindrance, and favor β-strand structure in the peptide itself because of the preference of tertiary amides for the trans conformation.

TABLE 4

Structure characterization, affinity and activity of the N-Methyl peptides

| Name | Sequence | Kd(µM) PR | Cell Death (MEC-1, 2 h) |
|---|---|---|---|
| PKHB1 | H-(D)K R F Y V V M W K (D)K-OH (SEQ ID No 27) | 22.6 µM | 78% |
| PKT7 | H-(D)K R F Y V ψ(CONMe)V M W K (D)K-OH (SEQ ID No 29) | NPD | 0% |
| PKT8 | H-(D)K R F Y ψ(CONMe)V V M W K (D)K-OH (SEQ ID No 30) | NPD | 0% |
| PKT9 | H-(D)K R F ψ(CONMe)Y V V M W K (D)K-OH (SEQ ID No 31) | NPD | 0% |
| PKT10 | H-(D)K R ψ(CONMe)F Y V V M W K (D)K-OH (SEQ ID No 32) | NPD | 0% |
| PKT11 | H-(D)K ψ(CONMe)R F Y V V M W K (D)K-OH (SEQ ID No 18) | 21.7 µM | 60% |
| PKT12 | H-(D)K R F Y V V M ψ(CONMe)W K (D)K-OH (SEQ ID No 42) | NPD | 0% |

TABLE 4-continued

Structure characterization, affinity and activity of the N-Methyl peptides

| Name | Sequence | Kd (μM) PR | Cell Death (MEC-1, 2 h) |
|---|---|---|---|
| PKT13 | H-(D)K R F Y V V ψ(CONMe)M W K (D)K-OH (SEQ ID No 33) | NPD | 0% |
| PKT14 | H-(D)K R F Y V V M W ψ(CONMe)K (D)K-OH (SEQ ID No 19) | NPD | 35% |
| PKT15 | H-(D)K ψ(CONMe)R F Y V V M W ψ(CONMe)K (D)K-OH (SEQ ID No 20) | 16 μM | 10% |
| PKT16 | H-(D)K ψ(CONMe)R F Y V V X W K (D)K-OH (SEQ ID No 21) | 12.1 μM | 68% |
| PKT17 | H-(D)K ψ(CONMe)R F Y V V L W K (D)K-OH (SEQ ID No 22) | 12 μM | 30% |
| PKT18 | H-(D)K ψ(CONMe)R F Y VV I W K (D)K-OH (SEQ ID No 23) | Not measured | 45% |

Moreover, the conformational propensity of each peptide was then examined by CD spectroscopy (FIG. 3). Far-UV CD spectra of the different peptides are dominated by a random coil signature, as inferred from the strong negative band around 195 nm. Deconvolution of the spectra leads to random coil contributions ranging from 80 to 90%. Peptides exhibit no helical propensity and a small β-sheet content can be observed only for the least soluble 4N1 and PKT1 peptides, suggesting that the b-structure arises from aggregated species. Interestingly, most peptides exhibit a small fraction of $P_{II}$ conformation, as suggested by the weak positive band near 220-225 nm.

Overall, CD spectroscopy indicates that these short linear peptides tend to be largely unstructured in aqueous solution. NMR spectroscopy was then used to probe the local conformations of individual amino acids, based on the analysis of NMR parameters such as $^1$Ha and $^{13}$Ca chemical shifts deviations (CSD), $^3J_{HN\text{-}H\alpha}$ coupling constants and NOEs.

The chemical shift deviations of $^1$Ha and $^{13}$Ca resonances are calculated as the differences between observed chemical shifts and corresponding values in random coil conformation for each amino acid. Significant CSDs can be used to detect the presence of helices, sheets or turns. The CSDs exhibit values close to zero for the different analogues (data not shown), confirming that these peptides do not adopt regular secondary structures in solution, as shown above by CD spectroscopy.

Example 3: Stability Studies on PKT16

3.1. Degradation in Human/Mouse Serum

To a mixture of 250 μL of human (or mouse) serum and 750 μL of RPMI 1640 were added 20 μL of the peptide DMSO stock solution at 10 mg/mL. The mixture was incubated at 37° C. Aliquots of 100 μL were removed from the medium at different time, mixed with 100 μL of acetonitrile and incubated at 4° C. for at least 15 min to precipitate all the serum proteins. After centrifugation at 12000 rpm for 2 min, 50 μL of the supernatant were transferred to an injection vial and analyzed by HPLC with a linear gradient of MeCN in water (5 to 95%+0.1% TFA). The relative concentrations of the remaining soluble peptides were calculated by integration of the absorbance at 220 nm as a function of the retention time (peak area).

3.2. Stability Under Proteinase K, Chymotrypsin and Trypsin Incubation

A 0.6 mL tube was charged with 180 μL of phosphate buffer pH 7.4, 10 μL of enzyme (0.05 mg/mL stock solution in phosphate buffer pH 7.4), 10 μL of peptide (10 mM stock solution in DMSO). The resulting reaction mixture was capped and incubated at room temperature for 3 hours. 20 μL of the crude reaction was quenched by addition of 180 μL of 50% water: 50% acetonitrile and was subjected to LC-MS analysis Method A or Method B according to the peptides.

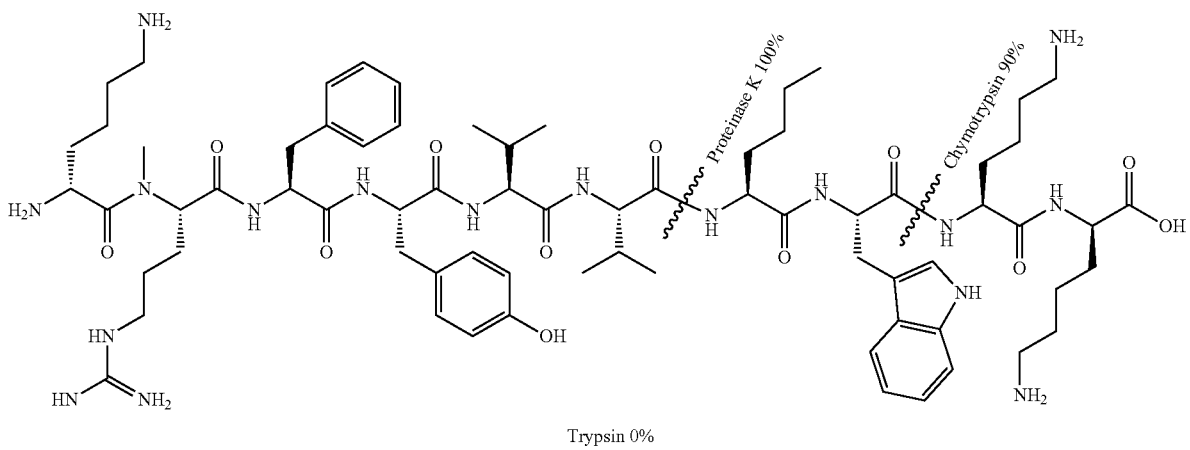

PKT16

Trypsin 0%

Example 4: Binding Affinity Measurements by Biolayer Interferometry (BI) and Microscale Thermophoresis (MT)

Protocols:

4.1.BI:

The binding affinities of peptides for a MEC-1 cells membrane preparation were measured by biolayer interferometry on an Octet RED96 System (Pall FortéBio Corp., Menlo Park, Calif.). This system monitors interference of light reflected from two sources (an internal reflection surface and the liquid/solid interface of a fiber optic sensor) to measure the rate of binding of molecules to the biosensor surface. MEC-1 cells membrane preparation is biotinylated with the EZ-Link NHS-PEG4-Biotin kit from Thermo-Scientific and excess biotin is removed using desalting column from Thermo-Scientific. Biotinylated membranes are then loaded onto SuperStreptavidin (SSA) biosensors (Pall FortéBio Corp.) at empirically determined concentrations. All affinity measurements were carried out in assay buffer (PBS with 0.05% Tween 20 and 1% DMSO) at 30° C. Typically, the biosensors were pre-equilibrated in PBS containing either biotinylated membranes or biocytine 100 µg/mL. Biosensors are then equilibrated in assay buffer for 10 min, brought to baseline in assay buffer for 60 sec. and transferred to wells containing peptide in dose-response (association for 120 sec. and dissociation for 300 sec.). The double reference with either membrane-loaded biosensors without any peptide dose-response or biocytine-loaded biosensors with each peptide dose-response were run in parallel for background signal double subtractions. Binding kinetics were calculated using the FortéBio Data Analysis v8.2 software.

4.2.MST:

For all experiments the concentration of the NT.115-labeled membrane was kept constant, while the concentrations of the ligand (peptide) was varied. After a short incubation time (5 min) the samples were loaded into MST premium glass capillaries and the MST analysis was performed using the Monolith NT.115.

TABLE 5

Reported apparent Kd values with associated standard deviations (=2; 3 or 4)

| Peptide | Kd (BI) | Kd (MST) |
|---|---|---|
| PKT16 | 74 µM | 1.6 µM |

Example 5: PKT16-FF: A New Potent Peptide

The replacement of the tyrosine residue in the "X2" position (i.e. accroding to formula (I)) of PKT16 by an alanine residue leads to an inactive peptide underlining the importance of this residue.

In order to assess the importance of the —OH group of this tyrosine, this tyrosine was replaced with a phenylalanine residue. Although this residue keeps the aromatic nucleus, it surprisingly proves to be more active than PKT16.

This new peptide was named PKT16-FF which is active from 25 microM over 6 hours as reported in FIG. 4. It was synthesized using common solide phase peptide synthesis technics as mentioned above.

To establish the importance of the hydroxyl (—OH) fragment on the aromatic ring of the tyrosine, the OH was replaced with different chemical functions "acceptor ($NO_2$, $NH_2$)" or hydrogen bond donor ($NH_2$). None of these peptides however led to an equivalent activity.

The major disadvantage of PKT16-FF is its low solubility in water (the peptide is more hydrophobic due to the absence of —OH), which results in a phenomenon of aggregation (depending on the nature of the solvent).

Example 6: PKT16 and PKT16-FF Analytical Comparison

Analytical Method A disclosed above was used here to characterize these peptides. The obtained values are summarized in table 6 hereunder.

TABLE 6

Analytical data for the peptides: retention times are indicated for LCM method A; Masses determined by LC-MS (ESI) are also shown:

| Peptide | Mw (g · mol$^{-1}$) | m/z (ESI) | $t_R$ (min) |
|---|---|---|---|
| PKT16 (sous forme amine $NH_2$ libre) | 1380.80 | 1381.8 $[M + H]^+$<br>691.1 $[M + 2H]^{2+}$<br>461.0 $[M + 3H]^{3+}$<br>346.0 $[M + 4H]^{4+}$ | 1.69 |
| PKT16-FF (sous forme amine $NH_2$ libre) | 1364.75 | 1365.8 $[M + H]^+$<br>691.1 $[M + 2H]^{2+}$<br>461.0 $[M + 3H]^{3+}$ | 1.78 |

The invention claimed is:

1. A compound or a pharmaceutical acceptable salt thereof of formula (III):

$$-A-B-X_1-X_2-X_3-X_4-X_5-X_6-C-D- \quad (III),$$

wherein

A is a (D)-Lysine, B is a (L)-Arginine, C is a (L)-Lysine, D is a (D)-Lysine;

A and B are linked to each other by a pseudopeptide bond —CO—NMe—; and $X_1$-$X_2$-$X_3$-$X_4$-$X_5$-$X_6$ is FYVVMW, FYVVXW (SEQ ID 1), FYVVIW (SEQ ID 2), FYVVKW (SEQ ID 3) or FYVVLW (SEQ ID 4), wherein X is norleucine.

2. The compound of claim 1, wherein the compound is H-(D)K Ψ(CONMe) R F Y V V M W K (D)K-OH (SEQ ID 18).

3. The compound of claim 1, wherein the compound is H-(D)K Ψ(CONMe) R F Y V V X W K (D)K-OH (SEQ ID 21).

4. The compound of claims 1, wherein the compound is H-(D)K Ψ(CONMe) R F Y V V LW K (D)K-OH (SEQ ID 22).

5. The compound of claim 1, wherein the compound is H-(D)K Ψ(CONMe) R F Y V V I W K (D)K-OH (SEQ ID 23).

\* \* \* \* \*